United States Patent
Eshoo et al.

(10) Patent No.: US 9,737,887 B2
(45) Date of Patent: Aug. 22, 2017

(54) INTEGRATED SAMPLE PREPARATION SYSTEMS AND STABILIZED ENZYME MIXTURES

(71) Applicant: Ibis Biosciences, Inc., Carlsbad, CA (US)

(72) Inventors: Mark Eshoo, San Diego, CA (US); John Picuri, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 14/629,047

(22) Filed: Feb. 23, 2015

(65) Prior Publication Data

US 2015/0231629 A1 Aug. 20, 2015

Related U.S. Application Data

(63) Continuation of application No. 13/925,355, filed on Jun. 24, 2013, now Pat. No. 8,961,899, which is a continuation-in-part of application No. 13/102,520, filed on May 6, 2011, now Pat. No. 8,470,261.

(60) Provisional application No. 61/331,910, filed on May 6, 2010.

(51) Int. Cl.
| | |
|---|---|
| *G01N 33/535* | (2006.01) |
| *G01N 33/50* | (2006.01) |
| *B01L 3/00* | (2006.01) |
| *C12Q 1/68* | (2006.01) |
| *B01L 7/00* | (2006.01) |

(52) U.S. Cl.
CPC ....... *B01L 3/5027* (2013.01); *B01L 3/502753* (2013.01); *B01L 7/52* (2013.01); *C12Q 1/6806* (2013.01); *B01L 2200/10* (2013.01); *B01L 2300/0672* (2013.01); *B01L 2300/0681* (2013.01); *B01L 2300/087* (2013.01); *B01L 2300/0816* (2013.01); *B01L 2300/0864* (2013.01); *B01L 2300/0867* (2013.01); *B01L 2300/0887* (2013.01); *B01L 2400/0481* (2013.01); *B01L 2400/0487* (2013.01); *B01L 2400/0683* (2013.01)

(58) Field of Classification Search
CPC ...... C12Q 1/6806; C12Q 1/6802; C12Q 1/68; C12Q 1/00; B01L 2400/0475; B01L 2400/04; B01L 2400/00; B01L 2200/10; B01L 2200/00; B01L 3/5027; B01L 3/502; B01L 3/50; B01L 3/00; B01L 3/502753
USPC .............. 422/502, 501, 500, 50; 506/40, 33; 435/188, 183
See application file for complete search history.

(56) References Cited

U.S. PATENT DOCUMENTS

| | | | |
|---|---|---|---|
| 5,876,992 A | 3/1999 | De Rosier et al. | |
| 5,912,148 A | 6/1999 | Eggerding | |
| 6,130,073 A | 10/2000 | Eggerding | |
| 6,210,891 B1 | 4/2001 | Nyren et al. | |
| 6,258,568 B1 | 7/2001 | Nyren | |
| 6,818,395 B1 | 11/2004 | Quake et al. | |
| 6,833,246 B2 | 12/2004 | Balasubramanian | |
| 6,911,345 B2 | 6/2005 | Quake et al. | |
| 6,969,488 B2 | 11/2005 | Bridgham et al. | |
| 7,115,400 B1 | 10/2006 | Adessi et al. | |
| 7,169,560 B2 | 1/2007 | Lapidus et al. | |
| 7,170,050 B2 | 1/2007 | Turner et al. | |
| 7,282,337 B1 | 10/2007 | Harris | |
| 7,302,146 B2 | 11/2007 | Turner et al. | |
| 7,313,308 B2 | 12/2007 | Turner et al. | |
| 7,329,492 B2 | 2/2008 | Hardin et al. | |
| 7,476,503 B2 | 1/2009 | Turner et al. | |
| 7,482,120 B2 | 1/2009 | Buzby et al. | |
| 7,501,245 B2 | 3/2009 | Quake et al. | |
| 7,668,697 B2 | 2/2010 | Volkov et al. | |
| 2004/0209299 A1* | 10/2004 | Pinter ................ | C12N 15/1093 435/6.12 |
| 2006/0094028 A1 | 5/2006 | Danna et al. | |
| 2006/0172314 A1* | 8/2006 | Song ................... | C12Q 1/6851 435/6.11 |
| 2008/0241951 A1 | 10/2008 | Battulga et al. | |

(Continued)

FOREIGN PATENT DOCUMENTS

| | | |
|---|---|---|
| JP | H09511653 A | 11/1997 |
| JP | H10503383 A | 3/1998 |

(Continued)

OTHER PUBLICATIONS

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.

(Continued)

*Primary Examiner* — Christine T Mui
(74) *Attorney, Agent, or Firm* — David A. Casimir; Casimir Jones, S.C.

(57) ABSTRACT

The present invention provides integrated sample preparation systems and stabilized enzyme mixtures. In particular, the present invention provides microfluidic cards configured for processing a sample and generating DNA libraries that are suitable for use in sequencing methods (e.g., next generation sequencing methods) or other suitable nucleic acid analysis methods. The present invention also provides stabilized enzyme mixtures containing an enzyme (e.g., an enzyme used in whole genome amplification), BSA, and a sugar. Such enzyme mixtures may be lyophilized and stored at room temperature without significant loss of enzyme activity for months.

15 Claims, 24 Drawing Sheets

(56) References Cited

U.S. PATENT DOCUMENTS

| | | | | |
|---|---|---|---|---|
| 2009/0148933 | A1* | 6/2009 | Battrell | B01F 11/0071 435/287.2 |
| 2009/0325276 | A1 | 12/2009 | Battrell et al. | |
| 2010/0035232 | A1 | 2/2010 | Ecker et al. | |

FOREIGN PATENT DOCUMENTS

| | | |
|---|---|---|
| JP | H11509094 A | 8/1999 |
| JP | 2000513940 A | 10/2000 |
| JP | 2002525125 A | 8/2002 |
| JP | 2003531592 A | 10/2003 |
| JP | 2004233356 A | 8/2004 |
| JP | 2006129727 A | 5/2006 |
| JP | 2007523627 A | 8/2007 |
| JP | 2009503555 A | 1/2009 |
| JP | 2009118847 A | 6/2009 |
| JP | 2009529883 A | 8/2009 |
| JP | 2012524268 A | 10/2012 |
| WO | WO-2007076549 A2 | 7/2007 |
| WO | WO-2007136715 A2 | 11/2007 |
| WO | WO-2008082712 A2 | 7/2008 |
| WO | WO-2008147382 A1 | 12/2008 |

OTHER PUBLICATIONS

Binladen J., et al., "The Use of Coded Pcr Primers Enables High-throughput Sequencing of Multiple Homolog Amplification Products by 454 Parallel Sequencing," Plos One, 2007, vol. 2 (2), pp. e197.

Blanco L., et al., "Highly Efficient Dna Synthesis by the Phage Phi 29 Dna Polymerase. Symmetrical Mode of Dna Replication," The Journal of Biological Chemistry, 1989, vol. 264 (15), pp. 8935-8940.

Clarke J., et al., "Continuous Base Identification for Single-Molecule Nanopore DNA Sequencing," Nature Nanotechnology, 2009, vol. 4 (4), pp. 265-270.

Dean F.B., et al., "Comprehensive Human Genome Amplification Using Multiple Displacement Amplification," Proceedings of the National Academy of Sciences, 2002, vol. 99 (8), pp. 5261-5266.

Extended European Search Report for Application No. EP11778444.7, mailed on Jul. 4, 2014, 5 pages.

Final Office Action mailed Jun. 24, 2014 for U.S. Appl. No. 13/925,355, filed Jun. 24, 2013.

Harris T.D., et al., "Single-molecule Dna Sequencing of a Viral Genome," Science, 2008, vol. 320 (5872), pp. 106-109.

Hoffmann C., et al., "Dna Bar Coding and Pyrosequencing to Identify Rare Hiv Drug Resistance Mutations," Nucleic Acids Research, 2007, vol. 35 (13), pp. e91.

International Search Report and Written Opinion for Application No. PCT/US2011/035597, mailed on Jan. 11, 2012, 13 pages.

Lizardi P.M., et al., "Mutation Detection and Single-molecule Counting using Isothermal Rolling-circle Amplification," Nature Genetics, 1998, vol. 19 (3), pp. 225-232.

MacLean D., et al., "Application of 'next-generation' Sequencing Technologies to Microbial Genetics," Nature Reviews Microbiology, 2009, vol. 7 (4), pp. 287-296.

Margulies M., et al., "Genome Sequencing in Microfabricated High-Density Picolitre Reactors," Nature, 2005, vol. 437 (7057), pp. 376-380.

McLaughlin S.F., et al., "Whole-Genome Resequencing with Short 25 Reads: Accurate Mutation Discovery with Mate Pairs and Quality Values", ASHG Annual Meeting, 2007.

Mikkelsen T.S., et al., "Genome-wide Maps of Chromatin State in Pluripotent and Lineage-committed Cells," Nature, 2007, vol. 448 (7153), pp. 553-560.

Mitsuya Y., et al., "Minority Human Immunodeficiency Virus Type 1 Variants in Antiretroviral-naive Persons with Reverse Transcriptase Codon 215 Revertant Mutations," Journal of Virology, 2008, vol. 82 (21), pp. 10747-10755.

Non-Final Office Action mailed Nov. 7, 2013 for U.S. Appl. No. 13/925,355, filed Jun. 24, 2013.

Non-Final Office Action mailed Oct. 18, 2012 for U.S. Appl. No. 13/102,520, filed May 6, 2011.

Notice of Allowance mailed May 8, 2013 for U.S. Appl. No. 13/102,520, filed May 6, 2011.

Notice of Allowance mailed Dec. 17, 2014 for U.S. Appl. No. 13/925,355, filed Jun. 24, 2013.

Notice of Allowance mailed Nov. 25, 2014 for U.S. Appl. No. 13/925,355, filed Jun. 24, 2013.

Notice of Rejection mailed Mar. 10, 2015 for Japanese Application No. JP2013509306 filed May 6, 2011.

Office Action mailed Mar. 10, 2014 for Canadian Application No. 2798635 filed May 6, 2011.

Office Action mailed Aug. 20, 2013 for Australian Application No. 2011249913 filed May 6, 2011.

Office Action mailed Oct. 30, 2013 for Chinese Application No. CN201100833729.3 filed May 6, 2011.

Second Office Action mailed Jul. 7, 2014 for Chinese Application No. 201100833729.3 filed May 6, 2011.

Shendure J., et al., "Accurate Multiplex Polony Sequencing of an Evolved Bacterial Genome," Science, 2005, vol. 309 (5741), pp. 1728-1732.

Simen B.B., et al., "Prevalence of Low Abundance Drug Resistant Variants by Ultra Deep Sequencing in Chronically HIV- 30 infected Antiretroviral (ARV) Naive Patients and the Impact on Virologic Outcomes," Antiviral Therapy, 2007, vol. 12, 16th International HIV Drug Resistance Workshop, Barbados, p. S149.

Telenius H., et al., "Degenerate Oligonucleotide-primed Pcr: General Amplification of Target Dna by a Single Degenerate Primer," Genomics, 1992, vol. 13 (3), pp. 718-725.

The Examination Search Report mailed Dec. 22, 2014 for Canadian Application No. CN2798635 filed May 6, 2011, 3 pages.

Third Office Action mailed Jan. 26, 2015 for Chinese Application No. CN201180033729.3 filed May 6, 2011.

Thomas R.K., et al., "SensitiveMutation-DetectioninHeterogeneousCancerSpecimensbyMassivelyParallelPicoliterReactorsequencing," Nature Medicine, 2006, vol. 12 (7), pp. 852-855.

Voelkerding K.V., et al., "Next-Generation Sequencing: from Basic Research to Diagnostics," Clinical Chemistry, 2009, vol. 55 (4), pp. 641-658.

Wang Y., et al., "A Novel Strategy to Engineer DNA Polymerases for Enhanced Processivity and Improved Performance in Vitro," Nucleic Acids Research, 2004, vol. 32 (3), pp. 1197-1207.

Zhang L., et al., "Whole Genome Amplification from a Single Cell: Implications for Genetic Analysis," Proceedings of the National Academy of Sciences of the United States of America, 1992, vol. 89 (13), pp. 5847-5851.

* cited by examiner

FIGURE 2

Disposable Microfluidic Sample Prep Development Cards

Design test and microfluidic sub-circuits:
- Cell lysis
- DNA Extraction
- Whole Genome Amplification
  - All reagents stabilized and contained on the cards

From prototype subcircuits to integrated injection molded devices

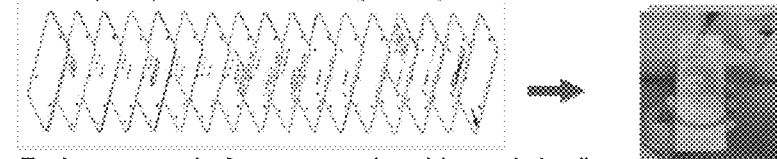

- Each component of an assay reduced to a subcircuit
- Sub-circuit results confirmed against gold standard assay
- Sub-circuits integrated for total assay performance
- Integrated prototype design converted to commercial design

Sample Purification:
Cartridge Fluidic Architecture

*Note: buffer packs, covers and pneumatics removed to enable visualization*

Step 1: Sample added to cartridge.

Step 3: Lysed mixture passed over capture filter and to waste chamber. Wash#1 passed over filter and to waste chamber.

Sample Purification:
Cartridge Fluidic Architecture

*Note: buffer packs, covers and pneumatics removed to enable visualization*

Step 4: Wash #2 passed through capture filter and to waste chamber. Filter air dried to remove wash #2.

Sample Purification:
Cartridge Fluidic Architecture

*Note: buffer packs, covers and pneumatics removed to enable visualization*

Elution Buffer from blister pack

Elution Bellows pumps elution buffer slowly over extraction membrane

Step 5: Elution buffer removes purified target from filter using elution bellows.

FIGURE 9

Results of final validation of lysis/extraction subcircuit. Inputs of 10,000 CFUs for *B. cereus* and *K. pneumoniae*, input of freshly grown culture for *S aureus*.

Reagent Stability

- Baseline stability
  - Extraction reagents
  - WGA buffer
  - WGA enzyme
- Accelerated aging
- Buffer stabilization
  - Storage in blister packs
- Enzyme stabilization
  - Lyophilization

Reagent Stabilization: WGA Enzyme Mix

- WGA enzyme mix is fragile
  - A mixture of three mesophilic enzymes
  - Stable for only 5 days at room temperature
  - No commercial vendor of stabilized WGA enzymes

- Lyophilization protects enzymes
  - Removes water
  - Replaces with protectants and stabilizers (excipients)
  - Increases shelf life
  - Decreases sensitivity to heat

FIGURE 15

Excipient Selection

- 25 excipient formulations were tested for compatibility with the WGA enzyme mix
  - Dialysis of enzymes into excipients
    - Glycerol needs to be removed for lyophilization
  - WGA using dialyzed enzymes to determine enzyme activity
  - Excipients 17-19 showed *increased* activity relative to fresh enzyme
  - Excipients 17 & 19 carried forward for small scale lyophilization testing WGA of 10 pg Klebsiella pneumoniae, 12 hr

On Card Liquid Reagents

* Advanced on-cartridge buffer pack development

* Materials selected for chemical compatibility with assay Wash and Lysis buffers

* Molded sharps designed to puncture packet and release stored reagent

* Extraction reagents stable for over 8 months based upon 4 months accelerated testing parameters

INTEGRATED SAMPLE PREPARATION SYSTEMS AND STABILIZED ENZYME MIXTURES

The present application is a continuation of U.S. patent application Ser. No. 13/925,355 filed Jun. 24, 2013, now U.S. Pat. No. 8,961,899, which is a continuation of U.S. patent application Ser. No. 13/102,520 filed May 6, 2011, now U.S. Pat. No. 8,470,261 issued Jun. 25, 2013, which claims priority to PCT Patent Application No. PCT/US2011/035597 filed May 6, 2011 and U.S. Provisional Patent application No. 61/331,910 filed May 6, 2010, the entirety of each of which is herein incorporated by reference in its entirety.

STATEMENT OF GOVERNMENT SUPPORT

This invention was made with United States Government support under contract number HDTRA-1-07-C-0096. The United States Government has certain rights in the invention.

FIELD OF THE INVENTION

The present invention relates to integrated sample preparation and sequencing systems and stabilized enzyme mixtures. In particular, the present invention provides microfluidic cards configured for processing a sample and generating DNA libraries that are suitable for use in sequencing methods (e.g., next generation sequencing methods) or other suitable nucleic acid analysis methods, where the output from these cards can be integrated with a DNA sequencing system providing an automated and integrated sample to sequence system. The present invention also provides stabilized enzyme mixtures containing an enzyme (e.g., an enzyme used in whole genome amplification), BSA, and a sugar. Such enzyme mixtures may be lyophilized and stored at room temperature without significant loss of enzyme activity for months.

BACKGROUND

Sequencing of DNA requires large amounts of extracted DNA for use in the preparation of a sequencing library. The process of culturing cells, lysing the cells, extracting DNA, fragmenting the DNA, ligating linkers, and purification of the sequencing template is a multi-step process that can take several days to be performed by a skilled research technician. The challenge of sequence based detection is that existing whole genome sequencing systems such as the Roche 454 require several days of sample preparation and several days for sequencing. FIG. 1 shows a flow chart demonstrating the lengthy process now involved in sample preparation for next-generation sequencing techniques, such as the Roche 454 method. As shown in this figure, it can take one day for sample pretreatment; cell lysis; nucleic acid extraction; and whole genome amplification (WGA). It can then take one to five days for generating DNA libraries, which involves the following steps: DNA fragmentation; DNA end repair; adaptor ligation; fragment immobilization; nick repair; single-strand DNA isolation; and emulsion PCR titration. Finally, it can then take one to four days to prepare the sample for sequencing and the sequencing itself using the following steps: bulk emulsion PCR; break emulsion PCR; purify PCR positive beads; prepare beads for sequencing; and performing the sequencing reaction.

What is needed are methods for preparing DNA sequencing libraries that are faster and easier to perform and the integration of these methods with the sequencers.

SUMMARY OF THE INVENTION

The present invention provides integrated sample preparation/nucleic acid sequencing systems and stabilized enzyme mixtures. In particular, the present invention provides microfluidic cards configured for processing a sample and generating DNA libraries that are suitable for use in sequencing methods (e.g., next generation sequencing methods) or other suitable nucleic acid analysis methods. The present invention also provides stabilized enzyme mixtures containing an enzyme (e.g., an enzyme used in whole genome amplification), BSA, and a sugar. Such enzyme mixtures may be lyophilized and stored at room temperature without significant loss of enzyme activity for months.

In certain embodiments, the present invention provides microfluidic cards comprising: a) a loading port configured for introduction of a biological sample; b) a fragmentation sub-circuit comprising: i) a reagent mixture configured for digesting nucleic acid (e.g., amplified nucleic acid) to generate fragmented nucleic acid, and/or ii) a fragmentation component configured for mechanically fragmenting nucleic acid to generate fragmented nucleic acid; and c) a linker ligation sub-circuit operably linked to said fragmentation sub-circuit, wherein said linker ligation sub-circuit comprises: i) nucleic acid linkers configured for use in sequencing methods or other methods, and ii) a ligation enzyme mixture configured for ligating said nucleic acid linkers to said fragmented nucleic acid to generate a nucleic acid sequencing library.

In certain embodiments, the present invention provides microfluidic cards comprising: a) a loading port configured for introduction of a biological sample; b) a cell lysis subcircuit; c) as nucleic acid extraction subcircuit; d) a nucleic acid amplification subcircuit wherein said amplification subcircuit comprises i) a target sequence specific amplification such as PCR or ii) a total nucleic acid amplification subcircuit such as whole genome amplification by multiple displacement amplification; e) a fragmentation sub-circuit comprising: i) a reagent mixture configured for digesting nucleic acid (e.g., amplified nucleic acid) to generate fragmented nucleic acid, and/or ii) a fragmentation component configured for physically fragmenting nucleic acid to generate fragmented nucleic acid; f) end polishing of fragmented nucleic acid; g) a linker ligation sub-circuit operably linked to said fragmentation sub-circuit, wherein said linker ligation sub-circuit comprises: i) nucleic acid linkers configured for use in sequencing methods or other methods, and ii) a ligation enzyme mixture configured for ligating said nucleic acid linkers to said fragmented nucleic acid to generate a nucleic acid sequencing library; h) methods for the removal of non-ligated or partially ligated nucleic acids; i) This can be performed enzymatically using for example exonucleases and or ii) by bind and elute extraction or iii) by affinity isolations using affinity tags as biotin labeled ligation products; i) final library purification by enzymatic or bind elute or affinity or size exclusion etc; j) integration with a sequencing system.

In particular embodiments, the microfluidics cards further comprise at least one additional sub-circuit selected from the following group: 1) a lysis sub-circuit (e.g., operably linked to said loading port) comprising: i) a mixing chamber and, ii) lysis buffer (e.g., in a sealed package); 2) a nucleic acid extraction sub-circuit (e.g., operably linked to both said lysis sub-circuit and a waste chamber), wherein said nucleic acid extraction sub-circuit comprises: i) a nucleic acid extraction component configured to bind nucleic acids present in a lysed sample, ii) a wash buffer (e.g., in a sealed package), iii) an elution buffer (e.g., in a sealed package), and iv) a pump component (e.g., configured for pumping the elution buffer over the nucleic acid extraction component to generate a mixture of extracted nucleic acids); 3) an amplification sub-circuit (e.g., operably linked to the nucleic acid extraction sub-circuit) comprising a stabilized enzyme mixture, wherein said stabilized enzyme mixture comprises at least one amplification-related enzyme useful for performing amplification on the extracted nucleic acid to generate amplified nucleic acid; and 4) a waste chamber;

In certain embodiments, the present invention provides microfluidic cards comprising: a) a loading port configured for introduction of a biological sample; b) an amplification sub-circuit (e.g., operably linked to the nucleic acid extraction sub-circuit) comprising a stabilized enzyme mixture, wherein said stabilized enzyme mixture comprises at least one amplification-related enzyme useful for performing whole genome amplification on nucleic acids to generate amplified nucleic acid.

In some embodiments, the present invention provides microfluidic cards comprising: a) a loading port configured for introduction of a biological sample; b) a waste chamber; c) a cell lysis sub-circuit operably linked to the loading port, wherein the cell lysis sub-circuit comprises: i) a mixing chamber and, ii) a first sealed package containing lysis buffer; wherein the lysis sub-circuit is configured to lyse the biological sample in the mixing chamber with the lysis buffer to generate a lysed sample; d) a nucleic acid extraction sub-circuit operably linked to both the cell lysis sub-circuit and the waste chamber, wherein the nucleic acid extraction sub-circuit comprises: i) a nucleic acid extraction component configured to bind nucleic acids present in the lysed sample, ii) a second sealed package containing wash buffer, iii) a third sealed package containing elution buffer, and iv) a pump component configured for pumping the elution buffer over the nucleic acid extraction component to generate a mixture of extracted nucleic acids; e) an amplification sub-circuit operably linked to the nucleic acid extraction sub-circuit, wherein the amplification sub-circuit comprises a stabilized enzyme mixture, wherein the stabilized enzyme mixture comprises at least one amplification-related enzyme useful for performing amplification on the extracted nucleic acid to generate amplified nucleic acid; f) a fragmentation sub-circuit operably linked to the amplification sub-circuit, wherein the fragmentation sub-circuit comprises: i) a reagent mixture configured for digesting the amplified nucleic acid to generate fragmented nucleic acid, and/or ii) a fragmentation component configured for mechanically fragmenting the amplified nucleic acid to generate fragmented nucleic acid; and g) a linker ligation sub-circuit operably linked to the fragmentation sub-circuit, wherein the linker ligation sub-circuit comprises: i) nucleic acid linkers (adaptors) configured for use in sequencing methods, and ii) a ligation enzyme mixture configured for ligating the nucleic acid linkers to the fragmented nucleic acid to generate a nucleic acid sequencing library.

In certain embodiments, the at least one amplification-related enzyme comprises an enzyme useful for performing whole genome amplification (WGA) (e.g., multiple displacement amplification), or useful for performing PCR, or useful for performing transcription mediated amplification (TMA). In some embodiments, the at least one amplification-related enzyme is selected from the group consisting of: Phi-29 polymerase, E. coli DNA polymerase I, inorganic pyrophosphatase, or any combination thereof. In certain embodiments, the amplification related enzymes are combined with linkers (adapters) that are used in next-generation sequencing, such as the next-generation sequencing methods described herein. In particular embodiments, the primer used for any amplification step (e.g., PCR) comprise linkers that are useful in next-generation sequencing methods (e.g., for tethering the amplicons to a solid support).

In particular embodiments, the stabilized enzyme mixture further comprises: i) BSA, ii) a sugar, and iii) at least one additional component selected from the group consisting of: an inorganic salt, a divalent metal cation, a buffering agent, an emulsifier, and a reducing agent. In other embodiments, the stabilized enzyme mixture further comprises: i) BSA, ii) a sugar, iii) an inorganic salt, iv) a divalent metal cation, v) a buffering agent, vi) an emulsifier, and vii) a reducing agent.

In some embodiments, the microfluidic cards further comprise: h) a purification sub-circuit operably linked to the linker ligation component, wherein the purification sub-circuit comprises a nucleic acid purification component, wherein the nucleic acid purification component comprises anchored nucleic acid sequences configured to hybridize to the linkers on the nucleic acid sequencing library. In other embodiments, the microfluidic cards further comprise an outlet port configured to allow a user to withdraw at least a portion of the nucleic acid sequencing library. In certain embodiments, the fragmentation subcircuit further comprises: at least one type of enzyme configured for polishing the ends of the fragmented nucleic acid. In particular embodiments, the linker ligation sub-circuit further comprises: at least one type of enzyme configured for polishing the ends of the nucleic acid sequencing library. In other embodiments, the stabilized enzyme mixture is present in a dried format. In some embodiments, the reagent mixture is present in a dried format.

In further embodiments, the pump component comprises a bellows. In other embodiments, the nucleic acid extraction components comprises a membrane. In additional embodiments, the nucleic acid extraction components comprises a filter. In particular embodiments, the microfluidics cards comprise a plurality of valves. In additional embodiments, the card is configured to operably link to, and be operated by, a processing instrument. In other embodiments, the microfluidics cards further comprise a plurality of air ports configured to operably link with a pneumatic interface on the processing instrument. In some embodiments, the nucleic acid linkers are configured for use in a sequencing method selected from the group consisting of: ABI SOLID, ILLUMINA SOLEXA, ROCHE 454, ION TORRENT, Lifetechnologies STARLITE, and PACIFIC BIOSCIENCES SMRT sequencing. In additional embodiments, the microfluidics cards further comprise a sensor configured to determine if the mixture of extracted nucleic acids requires amplification or not.

The sample preparation systems of the present invention may be integrated with any type of sequencing system (e.g., as a re-usable card or disposable card). In certain embodiments, the sample preparation systems of the present invention are integrated with ILLIMINA SOLEXA sequencers including HiSeq 2000, HiSeq 1000, HiScanSQ, Genome Analyzer IIx, MiSeq, where the sample preparation systems may be configured to work with the related Illumina software, such as the PIPELINE and/or CASAVA software packages. In other embodiments, the sample preparation systems of the present invention are integrated with the ROCHE 454 sequencers, including the Genome Sequencer FLX System and GS Junior System, where the sample preparation systems may be configured to work with the related GS Run Browser Software, GS De Novo Assembler Software, GS Reference Mapper Software, GS Amplicon Variant Analyzer Software, and the GS FLX Titanium Cluster. In some embodiments, the sample preparation systems of the present invention are integrated with the ION TORRENT sequencers, including the Ion Personal Genome Machine (PGM) sequencer, where the sample preparation systems may be configured to work with the related DNASTAR® SeqMan® NGen® Software, Partek® Genomics Suite™ Software, NextGENe® software for Ion PGM platform by SoftGenetics, or Avadis NGS Software. In additional embodiments, the sample preparation systems of the present invention are integrated with the PACIFIC BIOSCIENCES sequencers, including the PacBio RS sequencer, where the sample preparation systems may be configured to work with the related RS remote software, RS touch software, Primary Analysis software, SMRT Portal software, and SMRT View software.

In some embodiments, the present invention provides systems comprising: a microfluidic card as described herein; and b) a processing instrument configured to receive and operate the microfluidics card. In certain embodiments, the processing instrument comprises at least one component selected from: a pressure reservoir, a vacuum reservoir, at least one pump, a plurality of valves, at least one heater, a pneumatic interface, and an input-output computer connection. In additional embodiments, the processing instrument comprises: a pressure reservoir, a vacuum reservoir, at least one pump, a plurality of valves, at least one heater, a pneumatic interface, and an input-output computer connection.

In some embodiments, the present invention provides stabilized enzyme mixtures comprising, or consisting essentially of, or consisting of: a) at least one type of enzyme; b) bovine serum albumin (BSA); c) a sugar; and d) a buffering agent; and optionally water. In certain embodiments, the stabilized enzyme mixture further comprises, or consists essentially of, or consists of: at least one reagent selected from the group consisting of: an inorganic salt; a divalent metal cation; an emulsifier; and a reducing agent.

In particular embodiments, the present invention provides stabilized enzyme mixtures comprising, or consisting essentially of, or consisting of: a) at least one type of enzyme; b) bovine serum albumin (BSA); c) a sugar; d) an inorganic salt; e) a divalent metal cation; f) a buffering agent; g) an emulsifier; and h) a reducing agent.

In certain embodiments, the mixtures further comprise polyethylene glycol (PEG) (e.g., PEG-8000 or other weights). In further embodiments, the stabilized enzyme mixture is in an aqueous form or in a lyophilized form. In other embodiments, the stabilized enzyme mixture allows the enzyme to retain at least 70% of its activity (e.g., 70% ... 75% ... 80% ... 85% ... 90% ... 95% ... 100%) upon hydration at 20-25 degrees Celsius after storage for two months at 20-40 degrees Celsius.

In further embodiments, the BSA is present at a concentration of 0.05%-3.0% in the stabilized enzyme mixture (e.g., 0.05% ... 0.10% ... 0.5% ... 1.0% ... 2.0% ... 3.0%). In further embodiments, the sugar is present at a concentration of 5-35% of the stabilized enzyme mixture (e.g., 5% ... 15% ... 25% ... 35%). In other embodiments, the sugar is a non-reducing sugar. In further embodiments, the sugar is a disaccharide. In additional embodiments, the sugar is trehalose.

In some embodiments, the at least one type of enzyme comprises a mesophilic enzyme, a thermolabilze enzyme, or a thermophilic enzyme. In additional embodiments, the at least one type of enzyme comprises a polymerase. In particular embodiments, the polymerase is Phi-29 polymerase. In further embodiments, the polymerase is *E. coli* Polymerase I. In additional embodiments, the at least one type of enzyme comprises an inorganic pyrophosphatase. In certain embodiments, the inorganic pyrophosphatase is *Saccharomyces cerevisiae* inorganic pyrophosphatase. In additional embodiments, the at least one type of enzyme comprises: Phi-29 polymerase, *E. coli*. DNa Polymerase I, and *S. cerevisiae* inorganic pyrophosphatase.

In certain embodiments, the inorganic salt is present at a concentration of 1 mM-25 mM in the stabilized enzyme mixture (e.g., 1 mM ... 10 mM ... 17 mM ... 25 mM). In further embodiments, the inorganic salt is $(NH_4)_2SO_4$. In certain embodiments, the divalent metal cation is present at a concentration of 1 mM-30 mM in the stabilized enzyme mixture (e.g., 1 mM ... 10 mM ... 20 mM ... or 30 mM). In particular embodiments, the divalent metal cation is $MgCl_2$. In further embodiments, the buffering agent is present at a concentration of 10 mM-100 mM (e.g., 10 mM ... 35 mM ... 75 mM ... 100 mM). In some embodiments, the buffering agent is Tris.

In particular embodiments, the emulsifier is present at a concentration of 0.01%-0.15% in the stabilized enzyme mixture (e.g., 0.01% ... 0.1% ... 0.15%). In some embodiments, the emulsifier is Tween 40, Tween 20, or Tween 80. In additional embodiments, the reducing agent is present at a concentration of 1 mM-10 mM (e.g., 1 mM ... 5 mM ... 10 mM). In certain embodiments, the reducing agent is dithiothreitol (DTT).

In some embodiments, the present invention provides compositions for stabilizing an enzyme comprising, consisting essentially of, or consisting of: a) bovine serum albumin (BSA); b) a sugar; c) an inorganic salt; and optionally 1) a divalent metal cation; 2) a buffering agent; 3) an emulsifier; 4) a reducing agent; and 5) water.

In further embodiments, the present invention provides compositions comprising, or consisting essentially of, or consisting of: *E. coli* polymerase I and bovine serum albumin (BSA), wherein the composition is a lyophilized composition. In particular embodiments, the lyophilized composition allows the *E. coli* polymerase I to retain at least 70% of its activity (e.g., 70% ... 90% ... 100%) upon hydration at 20-25 degrees Celsius after storage for at least one, two, or three months at 20-40 degrees Celsius.

In certain embodiments, the present invention provides compositions comprising, or consisting essentially of, or consisting of: inorganic phosphatase and bovine serum albumin (BSA), wherein the composition is a lyophilized composition. In some embodiments, the lyophilized composition allows the inorganic phosphatase to retain at least 70% (e.g., 70% ... 90% ... 100%) of its activity upon hydration at 20-25 degrees Celsius after storage for two months at 20-40 degrees Celsius.

In further embodiments, the present invention provides methods of storing a lyophilized composition comprising: a) providing a lyophilized composition comprising, or consisting essentially of, or consisting of: i) at least one type of enzyme; ii) bovine serum albumin (BSA); iii) a sugar; iv) an inorganic salt; v) a divalent metal cation; vi) a buffering agent; vii) an emulsifier; and viii) a reducing agent; and b) storing the lyophilized composition at a storage temperature of 15-45 degrees Celsius for at least 15 days such that the at least one enzyme retains at least 70% of its activity upon hydration at 20-25 degrees Celsius. In further embodiments, the at least 15 days is at least 30 days (e.g., at least 30 days ... 60 days ... 90 days ... 120 days ... or longer). In certain embodiments, the storage temperature is 20-25 degrees Celsius. In some embodiments, the at least one enzyme is selected from *E. coli* polymerase I, Phi-29 polymerase, and inorganic pyrophosphatase.

In particular embodiments, the present invention provides methods of generating a stabilized enzyme composition comprising: a) providing: i) an aqueous composition comprising, or consisting essentially of, or consisting of: A) at least one type of enzyme; B) bovine serum albumin (BSA); C) a sugar; D) an inorganic salt; E) a divalent metal cation; F) a buffering agent; G) an emulsifier; and H) a reducing agent; and ii) a dializing membrane; and b) dialyzing the aqueous composition with the dialzying membrane into a solution comprising or consisting essentially of: i) the sugar; ii) the inorganic salt; iii) the divalent metal cation; iv) the buffering agent; v) the emulsifier; and vii) the reducing agent; c) freezing the aqueous composition to generate a frozen composition; and d) subjecting the frozen composition to high vacuum to remove water via sublimation such that a lyophilized composition is generated.

DESCRIPTION OF THE FIGURES

FIG. 2 shows an exemplary injected molded microfluidic card and the various layers that may make up a card. FIG. 2 also describes the first three sub-circuits of cell lysis, DNA extraction, and whole genome amplification.

FIG. 9 describes the three reference samples (*S. aureus; B. cereus*; and *K. pneumoniae*) that were used during development of embodiments of the present invention in order to evaluate the lysis and extraction steps.

FIG. 14 also describes the advantages of lyophilized mixtures of amplification enzymes, which are provided in Example I below.

FIG. 15 shows that many excipient formulations were tested (in Example 1) for compatibility with Phi-29, Polymerase I, and inorganic pyrophosphatase.

FIG. 21 describes how molded sharps on the microfluidic card can be used to puncture the blister packs and release their stored reagents.

DEFINITIONS

Figure 1:
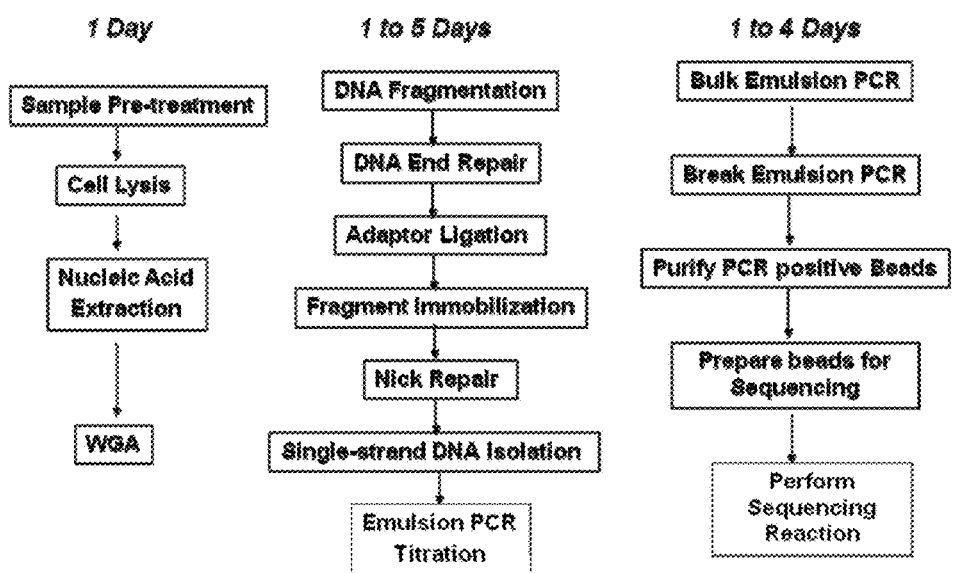
FIG. 1 shows a flow chart demonstrating the lengthy process now involved in sample preparation for next-generation sequencing techniques, such as the Roche 454 method.

As used herein, the phrase "microfluidic card" refers to a device, cartridge or "card" with selected internal channels, voids or other microstructures having at least one dimension on the order of 0.1 to 500 microns. Microfluidic devices may be fabricated from various materials using techniques such as laser stenciling, embossing, stamping, injection molding, masking, etching, and three-dimensional soft lithography. Laminated microfluidic devices are further fabricated with adhesive interlayers or by thermal adhesiveless bonding techniques, such as by pressure treatment of oriented polypropylene. The microarchitecture of laminated and molded microfluidic devices can differ. In certain embodiments, the microfluidic cards of the present invention are designed to interact or "dock" with a host instrument that provides a control interface and optional temperature and magnetic interfaces. The card, however, generally contains all biological reagents needed to perform the assay and requires only application of a sample or samples. These cards are generally disposable, single-use, and are generally manufactured with sanitary features to minimize the risks of exposure to biohazardous material during use and upon disposal.

The term "whole genome amplification" or "WGA" as used herein generally refers to a method for amplification of a limited DNA sample in a non-specific manner (unless targeted WGA is employed), in order to generate a new sample that is indistinguishable from the original but with a higher DNA concentration. The ideal whole genome amplification technique would amplify a sample up to a microgram level while maintaining the original sequence representation. The DNA of the sample may include an entire genome or a portion thereof. Degenerate oligonucleotide-primed PCR (DOP), primer extension PCR technique (PEP) and multiple displacement amplification (MDA), are examples of whole genome amplification methods.

The term "multiple displacement amplification" as used herein, refers to a non-PCR-based isothermal method based on the annealing of random hexamers (or non-random primers in targeted methods) to denatured DNA, followed by strand-displacement synthesis at constant temperature. It has been applied to small genomic DNA samples, leading to the synthesis of high molecular weight DNA with limited sequence representation bias. As DNA is synthesized by strand displacement, a gradually increasing number of priming events occur, forming a network of hyper-branched DNA structures. The reaction can be catalyzed by, for example, the Phi29 DNA polymerase or by the large fragment of the Bst DNA polymerase.

DETAILED DESCRIPTION

The present invention provides integrated sample preparation systems and stabilized enzyme mixtures. In particular, the present invention provides microfluidic cards configured for processing a sample and generating DNA libraries that are suitable for use in sequencing methods (e.g., next generation sequencing methods) or other suitable nucleic acid analysis methods. The present invention also provides stabilized enzyme mixtures containing an enzyme (e.g., an enzyme used in whole genome amplification), BSA, and a sugar. Such enzyme mixtures may be lyophilized and stored at room temperature without significant loss of enzyme activity for months.

I. Microfluidic Cards and Instruments

The present invention provides for the integration of several molecular biology processes/steps into a single integrated system using a microfluidic card. The integrated system can then, for example, be used to take samples (e.g., clinical, biological, environmental) and lyse the cells, extract the nucleic acids, amplify the extracted nucleic acids, (e.g., whole genome amplify), fragment the amplified nucleic acid, polish the DNA fragment ends, ligate linkers and purify the processed nucleic acid (e.g., a DNA sequencing library suitable for sequencing). The integrated process dramatically reduces the processing time, labor and improves the consistency of the process through the use of automation and quality controlled reagents that are integrated into the single use system.

The entire process can be integrated into single use microfluidic card that contains all the reagents needed to carry out the process. In some embodiments, the process wastes are also contained within the cards. The reagents can be stabilized so that the cards can be stored at room temperature for long periods of time. The cards generally contain a port where the resulting processed can be removed and used with a variety of DNA sequencing technologies such as Sanger sequencing, ABI SOLID, Illumina Solexa, Roche 454, Ion Torrent, ABI Starlite, PacBio SMRT, and other nucleic acid analysis techniques.

In certain embodiments, the microfluidic cards manufactured by Micronics Inc. and described in their patent publications are employed as part of the present invention. Micronics' PanNAT™ molecular diagnostic platform is described as a convenient, battery and/or main powered instrument capable of processing distinct cartridges, each designed to perform a single and/or multiplexed nucleic acid amplification assay. Each assay is fully integrated into the disposable cartridge that includes all necessary reagents. Only a small volume of biological sample is required for assay performance. A description of certain Micronics cards are provided in U.S. Patent Publication 20090325276, which is herein incorporated by reference in its entirety as if fully set forth herein. In certain embodiments, the microfluidic cards employed with the present invention are as described in the following paragraphs.

Microfluidic cards are formed from multiple subcircuits corresponding to independent assay modules, but integrated together in a single device or two or more interconnected devices. Each subcircuit in turn is preferably made up of microfluidic elements or components. Elements of these subcircuits may include microfluidic channels, tees, chambers, valves, filters, solid phase capture elements, isolation filters, pneumatic manifolds, blister packs (e.g., with reagent pouches), waste sequestration chambers, sanitary vents, bellows chambers, bellows pumps, optical windows, test pads, and microchannel-deposits of dehydrated reagents, optionally including buffers, solubilizers, and passivating agents. The subcircuits are generally fabricated of plastic, and may be made by lamination, by molding, and by lithography, or by a combination of these technologies.

The card devices are typically single-entry, meaning that after a sample or samples are introduced, the device is sealed so that any potential biohazard is permanently entombed in the card for disposal. However, in certain embodiments, the cards have an outlet port for removal of resulting DNA libraries. The cards are typically self-contained, in that any reagents needed for the assay are supplied with the device by the manufacturer. It is understood that microfluidic devices optionally may include RFID, microchips, bar codes, and labeling as an aid in processing analytical data and that the host instrument for card docking is optionally a smart instrument and can communicate patient data and test results to a network.

Microfluidic channels also termed "microchannels," are fluid channels having variable length, but one dimension in cross-section is less than 500 um. Microfluidic fluid flow behavior in a microfluidic channel is highly non-ideal and laminar and may be more dependent on wall wetting properties, roughness, liquid viscosity, adhesion, and cohesion than on pressure drop from end to end or cross-sectional area. The microfluidic flow regime is often associated with the presence of "virtual liquid walls" in the channel. Microfluidic channels are fluidly connected by "tees" to each other or to other process elements. Valves are formed in microfluidic channels, and may be check valves, pneumatic check valves, pinch valves, surface tension valves, and the like, as conventionally used.

The card devices generally contain an overlying pneumatic manifold that serves for control and fluid manipulation, although electronically activated valves could also be used. Air ports are connected to the pneumatic manifold, and generally activate bellows pumps. Where the valves are pneumatically actuated, air ports are also implicated. Air ports are sometimes provided with hydrophobic isolation filters (e.g., any liquid-impermeable, gas-permeable filter membrane) where leakage of fluid from within the device is undesirable and unsafe. Vents are not generally directly connected to the pneumatic manifold, but serve to equalize pressures within it.

Reaction chambers are provided on the microfluidic cards and can be any suitable shape, such as rectangular chambers, circular chambers, tapered chambers, serpentine channels, and various geometries for performing a reaction. These chambers may have windows for examination of the contents, as in detection chambers. Waste sequestration receptacles are generally provided on the microfluidic cards. Waste receptacles are optionally vented with sanitary hydrophobic membranes.

FIG. 2 shows an exemplary injected molded microfluidic card and the various layers that may make up a card. FIG. 2 also describes the first three sub-circuits of cell lysis, DNA extraction, and whole genome amplification.

Figure 3:
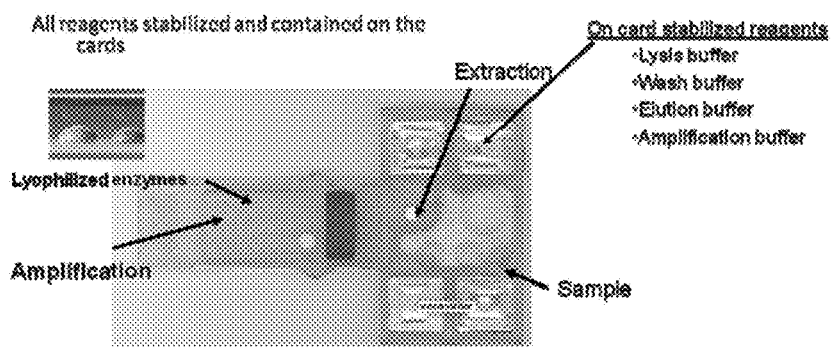
FIG. 3 shows an exemplary microfluidic card with various sub-circuits labeled, including a sample inlet port, a DNA extraction circuit, and an amplification circuit which includes lyophilized enzymes (e.g., such as those described below in Example 1).

FIG. 3 shows an exemplary microfluidic card with various sub-circuits labeled, including a sample inlet port, a DNA extraction circuit, and an amplification circuit which includes lypholized enzymes (e.g., such as those described below in Example 1).

Figure 4:
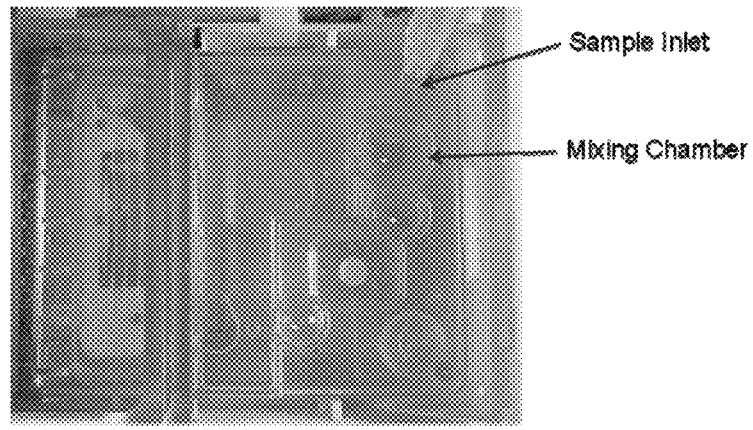
FIG. 4 shows step 1 of a sample preparation process utilizing a microfluidic card. This figure specifically shows a sample inlet port and a mixing chamber.

FIG. 4 shows step 1 of a sample preparation process utilizing a microfluidic card. This figure specifically shows a sample inlet port and a mixing chamber.

Figure 5:
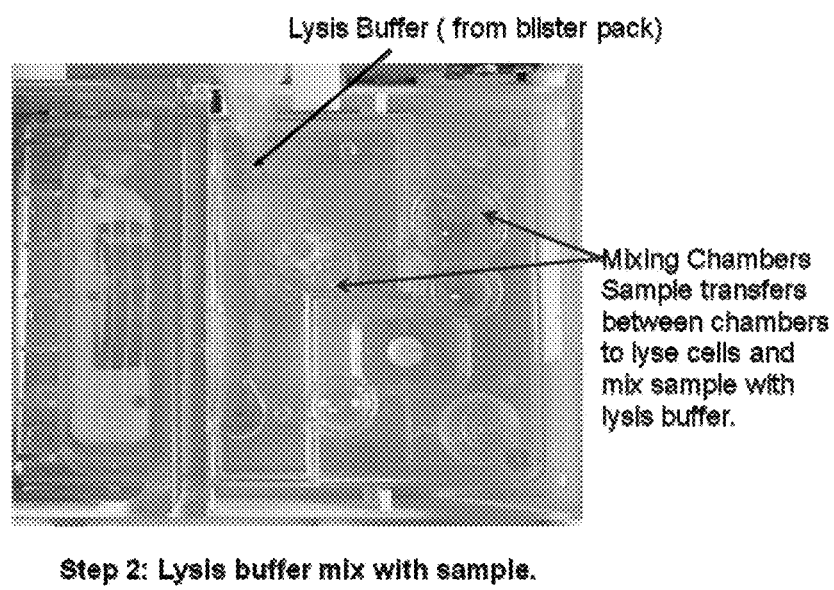
FIG. 5 shows step 2 which is a lysis step. Lysis buffer from a blister pack flows into a mixing chamber with cells from the sample such that the cells are lysed.

FIG. 5 shows step 2 which is a lysis step. Lysis buffer from a blister pack flows into a mixing chamber with cells from the sample such that the cells are lysed.

Figure 6:
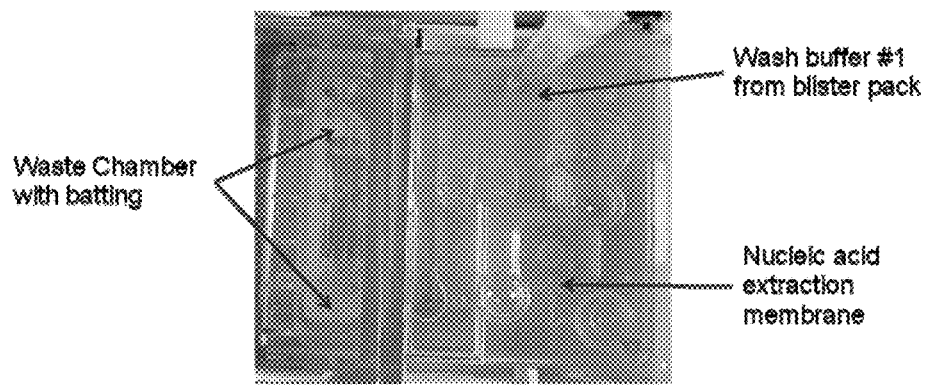
FIG. 6 shows step 3 where the lysed mixture is passed over a capture filter and then to a waste chamber. A first wash buffer from a blister pack is then passed over the filter before going into the waste chamber.

FIG. 6 shows step 3 where the lysed mixture is passed over a capture filter and then to a waste chamber. A first wash buffer from a blister pack is then passed over the filter before going to the waste chamber.

Figure 7:
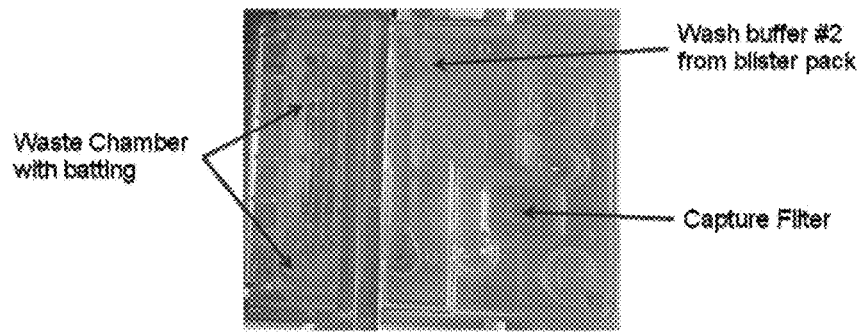
FIG. 7 shows step 4 where a second wash is passed through the capture filter and then on to the waste chamber. The filter is then air dried to remove the wash buffer.

FIG. 7 shows step 4 where a second wash is passed through the capture filter and then on to the waste chamber. The filter is then air dried to remove the wash buffer.

Figure 8:
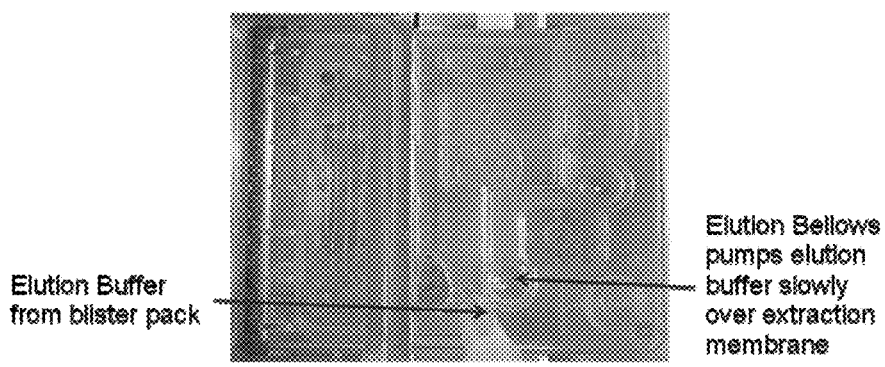
FIG. 8 shows step 5 where an elution buffer from a blister pack removes the purified nucleic acid from the filter using an elution bellows. The elution bellows pumps the elution buffer slowly over the filter.

FIG. 8 shows step 5 where an elution buffer from a blister pack removes the purified nucleic acid from the filter using an elution bellows. The elution bellows pumps the elution buffer slowly over the filter.

Figure 9:
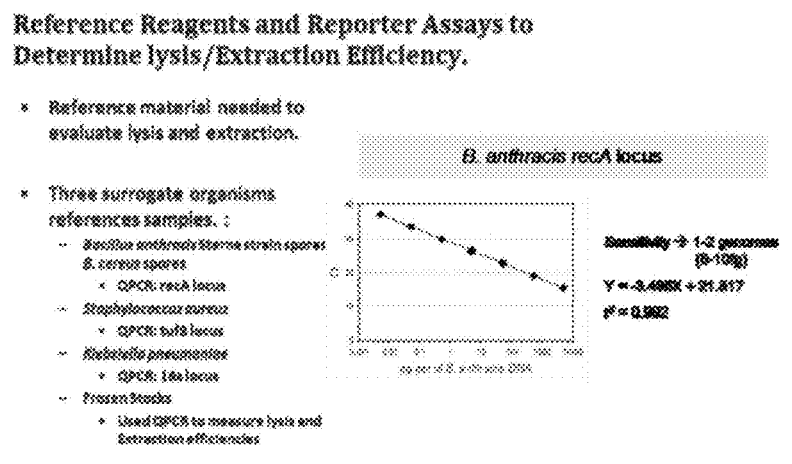

FIG. 9 describes the three reference samples (*S. aureus*; *B. cereus*; and *K. pneumoniae*) that were used during development of embodiments of the present invention in order to evaluate the lysis and extraction steps.

Figure 10:
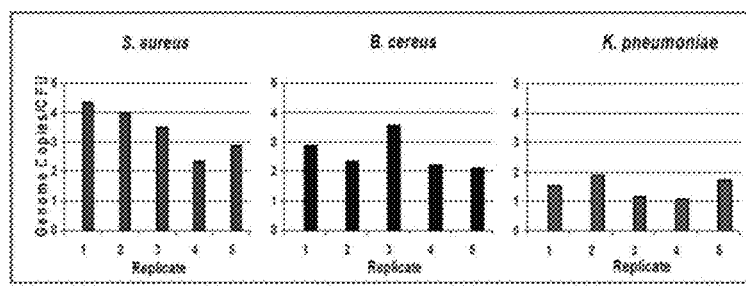
FIG. 10 shows the results of final validation of the lysis and extraction sub-circuits using *S. aureus; B. cereus*; and *K. pneumoniae*. The results shown are for inputs of 10,000 CFUs of *B. cereus* and *K. pneumoniae*, and freshly grown cultures of *S. aureus*.

FIG. 10 shows the results of final validation of the lysis and extraction sub-circuits using *S. aureus; B. cereus*; and *K. pneumoniae*. The results shown are for inputs of 10,000 CFUs of *B. cereus* and *K. pneumoniae*, and freshly grown cultures of *S. aureus*.

Figure 11:
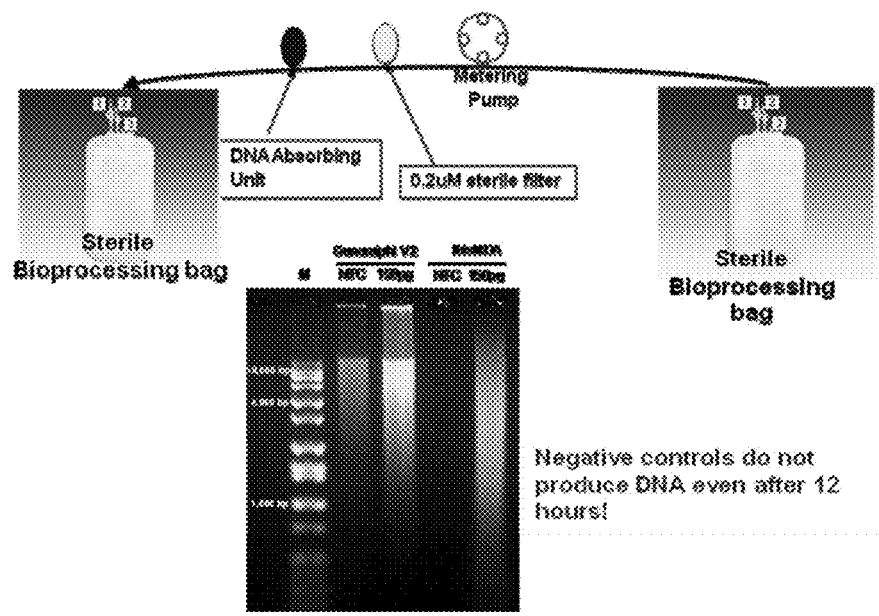
FIG. 11 shows production of contamination-free whole genome amplification reagents.

FIG. 11 production of contamination-free whole genome amplification reagents. In certain embodiments, reagents used for WGA are passed through a DNA absorbing unit and a 0.2 uM sterile filter. The results are purified reagents, where the negative controls do not produce DNA even after 12 hours.

Figure 12:
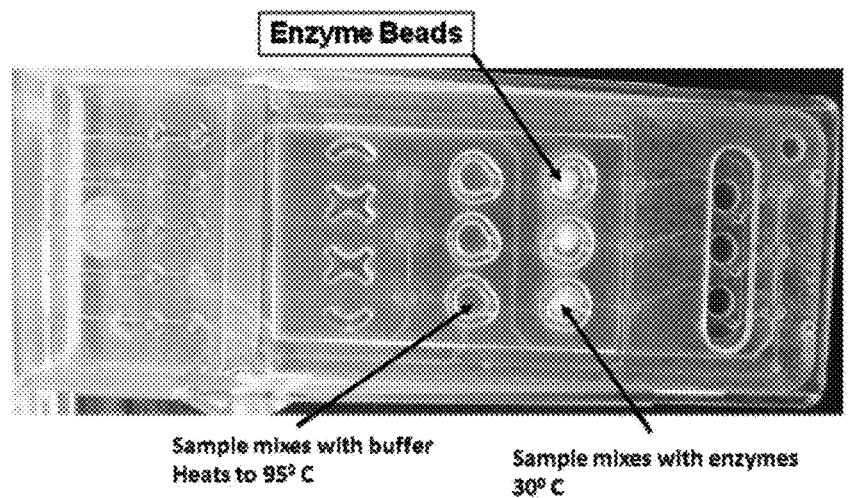
FIG. 12 shows step 6 where the purified nucleic acid sample is passed into the amplification sub-circuit with the reagents (including stabilized enzyme mixture lyophilized beads) inside the card.

FIG. 12 shows step 6 where the purified nucleic acid sample is passed into the amplification sub-circuit. In this circuit, whole genome amplification can be performed using a zone where the purified sample mixes with the amplification buffer (which can be the same as the elution buffer) and heated to 95 degrees Celsius and then moved to a reaction zone where it mixes with the amplification enzymes at 30 degrees Celsius. Preferably, the enzymes are lyophilized amplification enzymes that are part of stabilized enzyme mixtures as described in Example 1 below.

Figure 13:
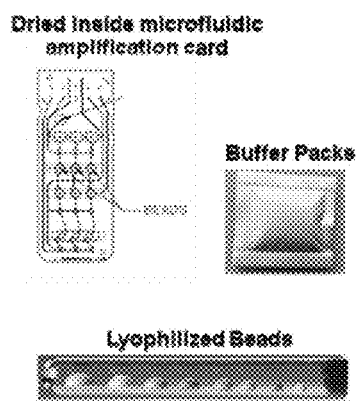
FIG. 13 shows an exemplary microfluidic card with the reagents (including stabilized enzyme mixture lyophilized beads) inside the card, as well as the configuration of the buffer packs.

FIG. 13 shows an exemplary microfluidic card with the reagents (including stabilized enzyme mixture lyophilized beads) dried inside the card, as well as the configuration of the buffer packs.

Figure 14:
FIG. 14 describes that prior art WGA enzyme mixtures were not stable during storage, with stability for only 5 days at room temperature.

FIG. 14 describes that prior art WGA enzyme mixtures were not stable during storage, with stability for only 5 days at room temperature. FIG. 14 also describes the advantages of lyophilized mixtures of amplification enzymes, which are provided in Example 1 below.

Figure 20:
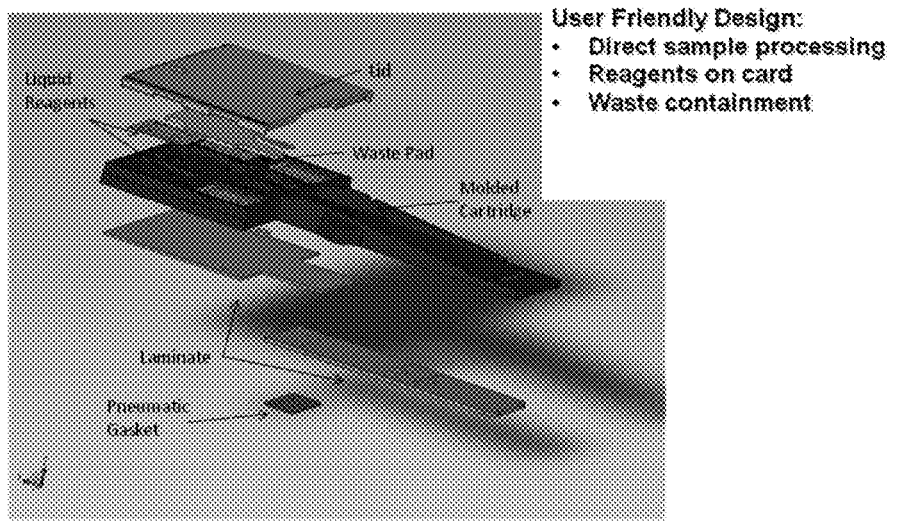
FIG. 20 shows an exemplary microfluidic card including a molded cartridge (with a waste pad and liquid reagents), a top lid, a laminate bottom, and a pneumatic gasket.

FIG. 20 shows an exemplary microfluidic card including a molded cartridge (with a waste pad and liquid reagents), a top lid, a laminate bottom, and a pneumatic gasket.

Figure 21:
FIG. 21 shows an image of an exemplary buffer blister pack.

FIG. 21 shows an image of an exemplary buffer blister pack. FIG. 21 describes how molded sharps on the microfluidic card can be used to puncture the blister packs and release their stored reagents.

Figure 22:
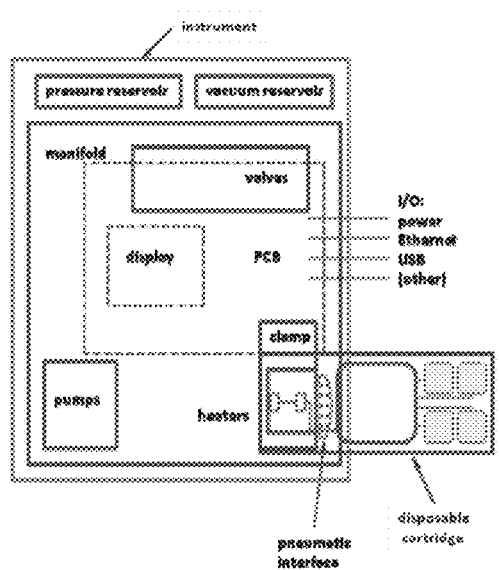
FIG. 22 shows a schematic of an exemplary processing instrument used to interface with and operate the microfluidic cards.

FIG. 22 shows a schematic of an exemplary processing instrument used to interface with and operate the microfluidic cards. As described in this figure, the processing instrument includes a processor to run the instrument; an input-output that may include a USB or Ethernet connection; an LCD screen to provide status to a user; and a touch screen for user control. The processing instrument may also include a pneumatic system containing air pumps, regulators, manifolds, pressure/vacuum reservoirs; and valves. The processing instrument may also include a card/cartridge interface with clamps, a pneumatic manifold, and heaters.

Figure 23:
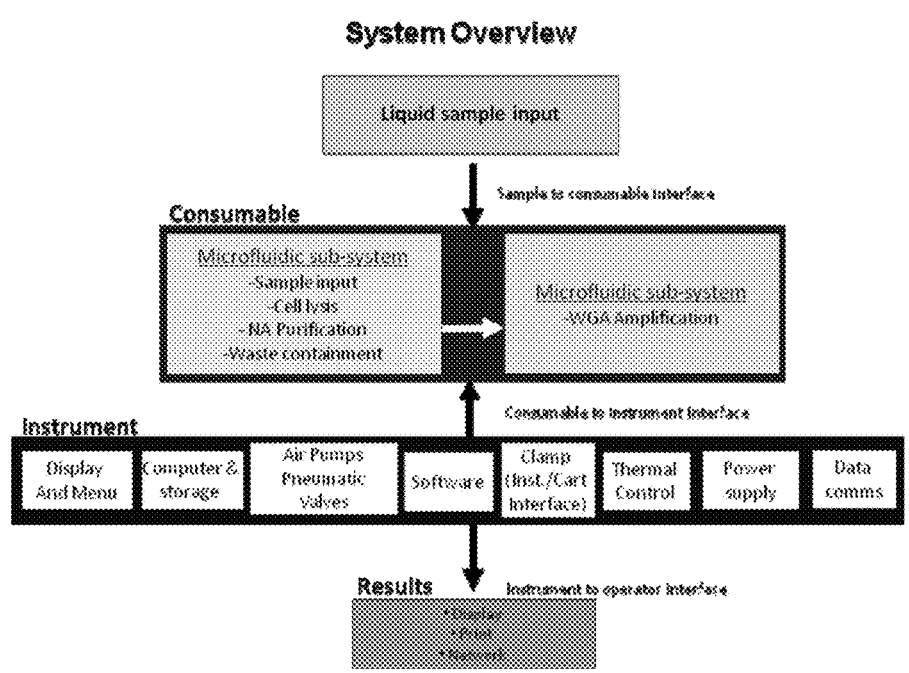
FIG. 23 shows an exemplary system overview of a consumable microfluidic card working with the processing instrument.

FIG. 23 shows an exemplary system overview of the consumable microfluidic card working with the processing instrument.

Figure 24:
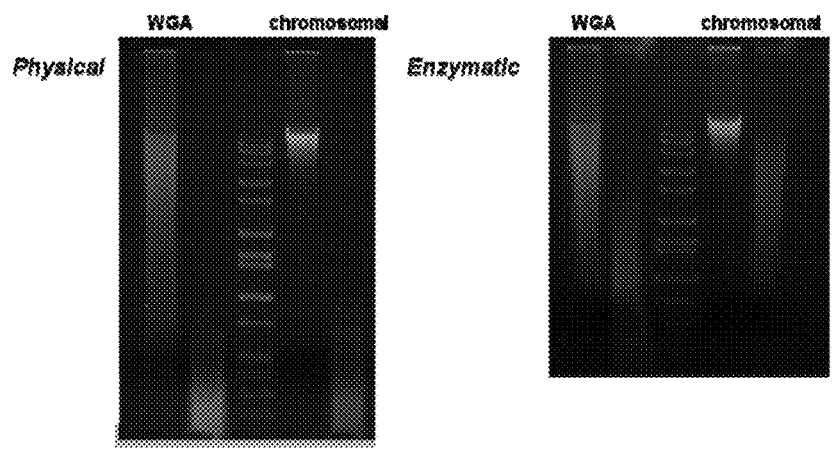
FIG. 24 shows exemplary results of fragmenting an amplified sample with either physical or enzymatic means.

FIG. 24 shows exemplary results of fragmenting a WGA amplified sample with either physical or enzymatic means. Such fragmentation may be performed in step 7 in the microfluidic card in a fragmentation sub-circuit. The amplified sample may be moved to the fragmentation sub-circuit and then be fragmented using mechanical shearing (e.g., by passing through an orifice in the fragmentation sub-circuit) or may be subjected to restriction enzymes. Fragmentation methods that may be employed include, but are not limited to, cleavage with restriction enzymes or cleavage primers, for example. Methods of using restriction enzymes and cleavage primers are well known to those with ordinary skill in the art. The ends of the fragments may then be polished with enzymes, such as Klenow fragment.

In certain embodiments, the next sub-circuit in the microfluidic cards is a linker ligation sub-circuit. In this sub-circuit, linkers are ligated to the ends of the fragmented nucleic acid. Preferably the linkers are those used in sequencing methods, such as those used in ABI SOLID, ILLUMINA SOLEXA, ROCHE 454, ION TORRENT, ABI STARLITE, and PACIFIC BIOSCIENCES SMRT sequencing. A description of these sequencing technologies and associated linkers is provided further below.

II. Whole Genome Amplification Methods

In certain embodiments, the microfluidic cards have reagents necessary, sufficient, or useful to perform whole genome amplification (WGA) in the amplification sub-circuit. It is noted that the present invention is not limited to WGA as the amplification technology, as any other type of suitable amplification technology (and corresponding reagents) maybe employed, such as PCR or TMA, both of which are well known in the art.

A. Non-Target WGA

In many fields of research such as genetic diagnosis, cancer research or forensic medicine, the scarcity of genomic DNA can be a severely limiting factor on the type and quantity of genetic tests that can be performed on a sample. One approach designed to overcome this problem is whole genome amplification (WGA). The objective is to amplify a limited DNA sample in a non-specific manner in order to generate a new sample that is indistinguishable from the original but with a higher DNA concentration. The aim of a typical whole genome amplification technique would be to amplify a sample up to a microgram level while respecting the original sequence representation.

The first whole genome amplification methods were described in 1992, and were based on the principles of the polymerase chain reaction. Zhang and coworkers (Zhang, L., et al. Proc. Natl. Acad. Sci. USA, 1992, 89: 5847-5851, herein incorporated by reference) developed the primer extension PCR technique (PEP) and Telenius and collaborators (Telenius et al., Genomics. 1992, 13(3):718-25, herein incorporated by reference) designed the degenerate oligonucleotide-primed PCR method (DOP-PCR) Zhang et al., 1992).

DOP-PCR is a method which uses Taq polymerase and semi-degenerate oligonucleotides (such as CGACTC-GAGNNNNATGTGG (SEQ ID NO: 1), for example, where N=A, T, C or G) that bind at a low annealing temperature at approximately one million sites within the human genome. The first cycles are followed by a large number of cycles with a higher annealing temperature, allowing for the amplification of the fragments that were tagged in the first step.

Multiple displacement amplification (MDA, also known as strand displacement amplification; SDA) is a non-PCR-based isothermal method based on the annealing of random hexamers to denatured DNA, followed by strand-displacement synthesis at constant temperature (Blanco et al., 1989, J. Biol. Chem. 264:8935-40, herein incorporated by reference). It has been applied to small genomic DNA samples, leading to the synthesis of high molecular weight DNA with limited sequence representation bias (Lizardi et al., Nature Genetics 1998, 19, 225-232; Dean et al., Proc. Natl. Acad. Sci. U.S.A. 2002, 99, 5261-5266; both of which are herein incorporated by reference). As DNA is synthesized by strand displacement, a gradually increasing number of priming events occur, forming a network of hyper-branched DNA structures. The reaction can be catalyzed by the Phi29 DNA polymerase or by the large fragment of the Bst DNA polymerase. The Phi29 DNA polymerase possesses a proof-reading activity resulting in error rates 100 times lower than the Taq polymerase.

In some embodiments, the reaction mixtures employed for the multiple displacement amplification include a plurality of polymerase enzymes. In some embodiments, the catalytic activities include 5'-3' DNA polymerase activity, 3'-5' exonuclease proofreading activity, and DNA repair activities such as, for example, 5'-3' excision repair activity. Examples of various polymerase enzymes include, but are not limited to, the following: Phi29, Klenow fragment, T4 polymerase, T7 polymerase, BstE polymerase, *E. coli* Pol I, Vent, Deep Vent, Vent exo-, Deep Vent exo-, KOD HiFi, Pfu ultra, Pfu turbo, Pfu native, Pfu exo-, Pfu exo-Cx, Pfu cloned, PROOFSTART (Qiagen), rTth, Tgo and Tfu Qbio. These polymerases are known and most are commercially available.

In other embodiments, other non-polymerase enzymes or accessory proteins are included in the MDA reaction mixtures such as, for example, helicase, gyrase, T4G32 and SSBP for example. In some embodiments, the reaction mixture for MDA includes pyrophosphatase which serves to convert pyrophosphate to phosphate. Pyrophosphate accumulates in the reaction mixture as a result of the amplification reaction (one equivalent of pyrophosphate is generated from each incorporated deoxynucleotide triphosphate added and is known to inhibit the amplification reaction). In some embodiments about 0.004 units of pyrophosphate is added to the reaction mixture.

B. Targeted WGA In certain embodiments, targeted whole genome amplification (TWGA) is employed as part of the present invention. Targeted WGA is described, for example, in U.S. Pat. Pub. 20100035232, herein incorporated by reference.

Target Genomes for Design of Targeted Whole Genome Amplification Primers

In some preferred embodiments, one or more target genomes are chosen. The choice of target genomes is dictated by the objective of the analysis. For example, if the desired outcome of the targeted whole genome amplification process is to obtain nucleic acid representing the genome of a biowarfare organism such as *Bacillus anthracis*, which is suspected of being present in a soil sample at the scene of a biowarfare attack, one may choose to select the genome of *Bacillus anthracis* as the one and only target genome. If, on the other hand, the desired outcome of the targeted whole genome amplification process is to obtain nucleic acid representing a group of bacteria, such as, a group of potential biowarfare agents, more than one target genome may be selected such as, a group comprising any or all of the following bacteria: *Bacillus anthracis, Francisella tularensis, Yersinia pestis, Brucella* sp., *Burkholderia mallei, Rickettsia prowazekii*, and *Escherichia coli* 0157. Likewise, a different genome or group of genomes could be selected as the target genome(s) for other purposes. For example, a human genome or mitochondrial DNA may be the target over common genomes found in a soil sample or other sample environments where a crime may have taken place. Thus, the current methods and compositions can be applied and the human genome (target) selectively amplified over the background genomes. Other examples could include the genomes of group of viruses that cause respiratory illness, pathogens that cause sepsis, or a group of fungi known to contaminate households.

Background Genomes for Design of Targeted Whole Genome Amplification Primers

Background genomes may be selected based on the likelihood of the nucleic acid of certain organisms being present. For example, a soil sample which was handled by a human would be expected to contain nucleic acid representing the genomes of organisms including, but not limited to: *Homo sapiens, Gallus gallus, Guillardia theta, Oryza sativa, Arabidopsis thaliana, Yarrowia lipolytica, Saccharomyces cerevisiae, Debaryomyces hansenii, Kluyveromyces lactis, Schizosaccharmyces pom, Aspergillus fumigatus, Cryptococcus neoformans, Encephalitozoon cuniculi, Eremothecium gossypii, Candida glabrata, Apis mellifera, Drosophila melanogaster, Tribolium castaneum, Anopheles gambiae*, and *Caenorhabditis elegans*. Any or all of these genomes are appropriate to estimate as background genomes in the sample. The organisms actually in any particular sample will vary for each sample based upon the source and/or environment. Therefore, background genomes may be selected based upon the identities of organisms actually present in the sample. The composition of a sample can be determined using any of a number of techniques known to those ordinarily skilled in the art. In a further embodiment, the primers can be designed based upon actual identification of one or more background organisms in the sample, and based upon likelihood of any further one or more background organisms being in the sample.

Identification of Unique Genome Sequence Segments as Primer Hybridization Sites

Once the target and background genomes of a sample are determined, the next step is to identify genome sequence segments within the target genome which are useful as primer hybridization sites. The efficiency of a given targeted whole genome amplification is dependent on effective use of primers. To produce an amplification product representative of a whole genome, the primer hybridization sites should have appropriate separation across the length of the genome. Preferably the mean separation distance between the primer hybridization sites is about 1000 nucleobases or less. More preferably the mean separation is about 800 nucleobases in length or less. Even more preferably, the mean separation is about 600 nucleobases in length or less. Most preferably, the mean separation between primer hybridization sites is about 500 nucleobases in length or less.

One with ordinary skill in the art will recognize that effective priming for whole genome amplification depends upon several factors such as the fidelity and processivity of the polymerase enzyme used for primer extension. A longer mean separation distance between primer hybridization sites becomes more acceptable if the polymerase enzyme has high processivity. This indicates that the polymerase binds tightly to the nucleic acid template. This is a desirable characteristic for targeted whole genome amplification because it enables the polymerase to remain bound to the template nucleic acid and continue to extend the complementary nucleic acid strand being synthesized. Examples of polymerase enzymes having high processivity include, but are not limited to Phi29 polymerase and Taq polymerase. Protein engineering strategies have been used to produce high processivity polymerase enzymes, for example, by covalent linkage of a polymerase to a DNA-binding protein (Wang et al., Nucl. Acids Res., 2004, 32(3) 1197-1207, herein incorporated by reference). As polymerases with improved processivity become available, longer mean separation distances, even greatly exceeding 1000 nucleobases may be acceptable for targeted whole genome amplification.

Hybridization Sensitivity and Selectivity

For the purpose of targeted whole genome amplification, the choice of length of the primer hybridization sites (genome sequence segments) and the lengths of the corresponding primers hybridizing thereto, preferably will balance two factors; (1) sensitivity, which indicates the frequency of binding of a given primer to the target genome, and (2) selectivity, which indicates the extent to which a given primer hybridizes to the target genome with greater frequency than it hybridizes to background genomes. Generally, longer primers tend toward greater selectivity and lesser sensitivity while the converse holds for shorter primers. Preferably primers of about 5 to about 13 nucleobases in length are useful for targeted whole genome amplification; however, primer lengths falling outside of this range can be used as well. One will recognize that this range comprises primers having lengths of 5, 6, 7, 8, 9, 10, 11, 12 and 13 nucleobases. Primer size affects the balance between selectivity of the primer and sensitivity of the primer. Optimal primer length is determined for each sample with this balance in mind. Primers with lengths less than 5 nucleobases or greater than 13 nucleobases are also useful if the selectivity and sensitivity can be optimally maintained for that sample. Choosing a plurality of primers having various lengths provide broad priming across the target genome sequence(s) while also providing preferential binding of the primers to the target genome sequence(s) relative to the background genome sequences.

Selection Threshold Criteria

In some embodiments, it is preferable to determine a suitable sub-set of the total unique genome sequence segments in order to reduce the total number of primers in the targeted whole genome amplification set in order to reduce the costs and complexity of the primer set. In some embodiments, determination of the suitable sub-set of unique genome sequence segments entails choosing one or more threshold criteria which indicate a useful and practical cut-off point for sensitivity and/or selectivity of a given genome sequence segment. Examples of such criteria include, but are not limited to, a selected threshold frequency of occurrence (a frequency of occurrence threshold value), and a selected selectivity ratio (a selectivity ratio threshold value).

In some embodiments, it is useful to rank the total unique genome sequence segments according to the criteria. For example, the total unique genome sequence segments are ranked according to frequency of occurrence with the #1 rank indicating the greatest frequency of occurrence and the lowest rank indicating the lowest frequency of occurrence. A threshold frequency of occurrence can then be chosen from the ranks. The threshold frequency of occurrence serves as the dividing line between members of the sub-set chosen for further analysis and the members that will not be further analyzed.

Design of Primers

The primers that are designed to hybridize to the selected genome sequence segments are preferably 100% complementary to the genome sequence segments. In other embodiments, the primers that are designed to hybridize to the selected genome sequence segments are at least about 70% to about 100% complementary to the genome sequence segments, or any whole or fractional number therebetween. In general terms, design of primers for hybridization to selected nucleic acid sequences is well known to those with skill in the art and can be aided by commercially available computer programs. It is generally preferable to design a given primer such that it is the same length as the genome sequence segment which was analyzed and chosen as a primer hybridization site. However, in some cases it may be advantageous to alter the length of the primer relative to the primer hybridization site. For example, if the primer is analyzed and found to have an unfavorable melting temperature and would benefit from elongation at the 5' or 3' end to produce a primer having an improved affinity for the target genome sequence. The length of the primer can be either increased or decreased. One with ordinary skill will recognize that alteration of the primer length also alters the primer hybridization site so that it no longer identical to the originally selected genome sequence segment. In some cases, it may be beneficial to analyze the genome sequence segment which corresponds to the hybridization site of a given length-altered primer. This analysis may be done by examination of data including but not limited to: frequency of occurrence and selectivity ratio and may also be done by actual in vitro testing of the length-altered primer.

In some embodiments, in cases where it may be advantageous to design a primer to be less than 100% complementary to its corresponding genome sequence segment, it is also advantageous to examine the complement of the re-calculate selection criteria (such as frequency of occurrence and selectivity ratio) for a hypothetical genome sequence segment that is 100% complementary to the primer which is less than 100% complementary to its corresponding original genome sequence segment. If the selection criteria are unfavorable, it would be advantageous to consider design of an alternate primer sequence having improved selection criteria.

III. Sequencing Technologies

As described above, embodiments of the present invention involve sequencing the DNA library that is generated with the microfluidics cards. The present invention is not limited by the the type of sequencing method employed. Exemplary sequencing methods are described below.

Illustrative non-limiting examples of nucleic acid sequencing techniques include, but are not limited to, chain terminator (Sanger) sequencing and dye terminator sequencing. Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A set of methods referred to as "next-generation sequencing" techniques have emerged as alternatives to Sanger and dye-terminator sequencing methods (Voelkerding et al., *Clinical Chem.*, 55: 641-658, 2009; MacLean et al., *Nature Rev. Microbiol.*, 7: 287-296; each herein incorporated by reference in their entirety). Most current methods describe the use of next-generation sequencing technology for de novo sequencing of whole genomes to determine the primary nucleic acid sequence of an organism. In addition, targeted re-sequencing (deep sequencing) allows for sensitive mutation detection within a population of wild-type sequence. Some examples include recent work describing the identification of HIV drug-resistant variants as well as EGFR mutations for determining response to anti-TK therapeutic drugs. Recent publications describing the use of bar code primer sequences permit the simultaneous sequencing of multiple samples during a typical sequencing run including, for example: Margulies, M. et al. "Genome Sequencing in Microfabricated High-Density Picoliter Reactors", Nature, 437, 376-80 (2005); Mikkelsen, T. et al. "Genome-Wide Maps of Chromatin State in Pluripotent and Lineage-Committed Cells", Nature, 448, 553-60 (2007); McLaughlin, S. et al. "Whole-Genome Resequencing with Short Reads: Accurate Mutation Discovery with Mate Pairs and Quality Values", ASHG Annual Meeting (2007); Shendure J. et al. "Accurate Multiplex Polony Sequencing of an Evolved Bacterial Genome", Science, 309, 1728-32 (2005); Harris, T. et al. "Single-Molecule DNA Sequencing of a Viral Genome", Science, 320, 106-9 (2008); Simen, B. et al. "Prevalence of Low Abundance Drug Resistant Variants by Ultra Deep Sequencing in Chronically HIV-infected Antiretroviral (ARV) Naïve Patients and the Impact on Virologic Outcomes", 16th International HIV Drug Resistance Workshop, Barbados (2007); Thomas, R. et al. "Sensitive Mutation Detection in Heterogeneous Cancer Specimens by Massively Parallel Picoliter Reactor Sequencing", Nature Med., 12, 852-855 (2006); Mitsuya, Y. et al. "Minority Human Immunodeficiency Virus Type 1 Variants in Antiretroviral-Naïve Persons with Reverse Transcriptase Codon 215 Revertant Mutations", J. Vir., 82, 10747-10755 (2008); Binladen, J. et al. "The Use of Coded PCR Primers Enables High-Throughput Sequencing of Multiple Homolog Amplification Products by 454 Parallel Sequencing", PLoS ONE, 2, e197 (2007); and Hoffmann, C. et al. "DNA Bar Coding and Pyrosequencing to Identify Rare HIV Drug Resistance Mutations", Nuc. Acids Res., 35, e91 (2007), all of which are herein incorporated by reference.

Compared to traditional Sanger sequencing, next-gen sequencing technology produces large amounts of sequencing data points. A typical run can easily generate tens to hundreds of megabases per run, with a potential daily output reaching into the gigabase range. This translates to several orders of magnitude greater than a standard 96-well plate, which can generate several hundred data points in a typical multiplex run. Target amplicons that differ by as little as one nucleotide can easily be distinguished, even when multiple targets from related species are present. This greatly enhances the ability to do accurate genotyping. Next-gen sequence alignment software programs used to produce consensus sequences can easily identify novel point mutations, which could result in new strains with associated drug resistance. The use of primer bar coding also allows multiplexing of different patient samples within a single sequencing run.

Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color and thus identity of each probe corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing in employed (see, e.g., Astier et al., J Am Chem Soc. 2006 Feb. 8; 128(5):1705-10, herein incorporated by reference). The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is exceedingly sensitive to the size of the nanopore. If DNA molecules pass (or part of the DNA molecule passes) through the nanopore, this can create a change in the magnitude of the current through the nanopore, thereby allowing the sequences of the DNA molecule to be determined. The nanopore may be a solid-state pore fabricated on a metal and/or nonmetal surface, or a protein-based nanopore, such as α-hemolysin (Clarke et al., Nat. Nanotech., 4, Feb. 22, 2009: 265-270).

HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No.

7,501,245; U.S. Pat. No. 6,818,395; U.S. Pat. No. 6,911,345; U.S. Pat. No. 7,501,245; each herein incorporated by reference in their entirety) is the first commercialized single-molecule sequencing platform. This method does not require clonal amplification. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run. Other emerging single molecule sequencing methods real-time sequencing by synthesis using a VisiGen platform (Voelkerding et al., *Clinical Chem.*, 55: 641-658, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition. Another real-time single molecule sequencing system developed by Pacific Biosciences (Voelkerding et al., *Clinical Chem.*, 55: 641-658, 2009; MacLean et al., *Nature Rev. Microbiol.*, 7: 287-296; U.S. Pat. No. 7,170,050; U.S. Pat. No. 7,302,146; U.S. Pat. No. 7,313,308; U.S. Pat. No. 7,476,503; all of which are herein incorporated by reference) utilizes reaction wells 50-100 nm in diameter and encompassing a reaction volume of approximately 20 zeptoliters ($10 \times 10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters (10-21 liters). At this volume, the activity of a single molecule can be detected amongst a background of thousands of labeled nucleotides.

The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

As the DNA polymerase incorporates complementary nucleotides, each base is held within the detection volume for tens of milliseconds, which is orders of magnitude longer than the amount of time it takes a nucleotide to diffuse in and out of the detection volume. During this time, the engaged fluorophore emits fluorescent light whose color corresponds to the base identity. Then, as part of the natural incorporation cycle, the polymerase cleaves the bond holding the fluorophore in place and the dye diffuses out of the detection volume. Following incorporation, the signal immediately returns to baseline and the process repeats.

Unhampered and uninterrupted, the DNA polymerase continues incorporating bases at a speed of tens per second. In this way, a completely natural long chain of DNA is produced in minutes. Simultaneous and continuous detection occurs across all of the thousands of ZMWs on the SMRT chip in real time. Researchers at PacBio have demonstrated this approach has the capability to produce reads thousands of nucleotides in length.

EXAMPLES

The following Examples are presented in order to provide certain exemplary embodiments of the present invention and are not intended to limit the scope thereof.

Example 1

Stabilized Enzyme Mixtures

Figure 16:
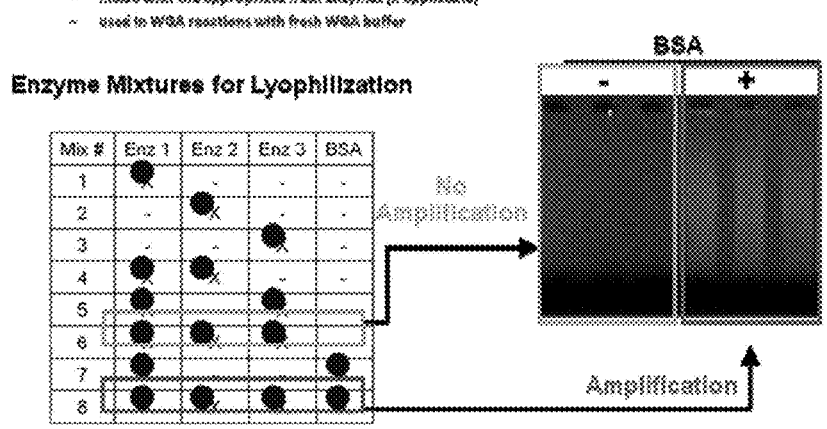
FIG. 16 shows results from Example 1 indicating that BSA is an important component for stabilizing amplification enzymes.

This example describes the development of stabilized enzyme mixtures that are useful in methods such as whole genome amplification (WGA). As described in FIG. 15, many excipient formulations were tested for compatibility with the WGA of Phi-29, Polymerase I, and inorganic pyrophosphatase. It was found that 16 proprietary stabilization formulations (called excipients) were not useful at successfully stabilizing the enzymes generally used in WGA. It was found that BSA was an important component for stabilizing these enzymes, as shown in FIG. 16.

One preferred excipient that was developed is called "Ibis Formula 33." A description of how to make this formulation is as follows. A mixture of 8968 u/ml Phi-29 polymerase (Monserate), 180 u/ml Polymerase I (Epicentre Biotechnologies), 3.6 u/ml Inorganic Pyrophosphatase (U.S. Biochemical) is mixed 1:1 with a solution containing 20% trehalose, 10 mM $(NH_4)_2SO_4$, 12 $MgCl_2$, 50 mM Tris pH 7.6, 0.05% Tween 40, 4 mM DTT and BSA at a level to achieve a final concentration of 0.25% (due to volume changes during dialysis there is a higher concentration of BSA during dialysis so that the solution can be brought up to the correct final volume post-dialysis.) This mixture is dialyzed using a 30 KDa dialysis membrane into a solution containing 20% trehalose, 10 mM $(NH_4)_2SO_4$, 12 $MgCl_2$, 50 mM Tris pH 7.6, 0.05% Tween 40 and 4 mM DTT for 4 hours at room temperature.

The dialyzed enzyme mixture is then removed from the dialysis membrane and brought up to the correct final volume (the level of dilution during the dialysis/dilution process controls how much enzyme is present per lyophilized unit) using a solution containing 20% trehalose, 10 mM $(NH_4)_2SO_4$, 12 $MgCl_2$, 50 mM Tris pH 7.6, 0.05% Tween 40 and 4 mM DTT. This solution is then aliquoted into appropriate volumes, frozen and subjected to a high vacuum to remove the water via sublimation to generate a lypilized composition.

Figure 17:
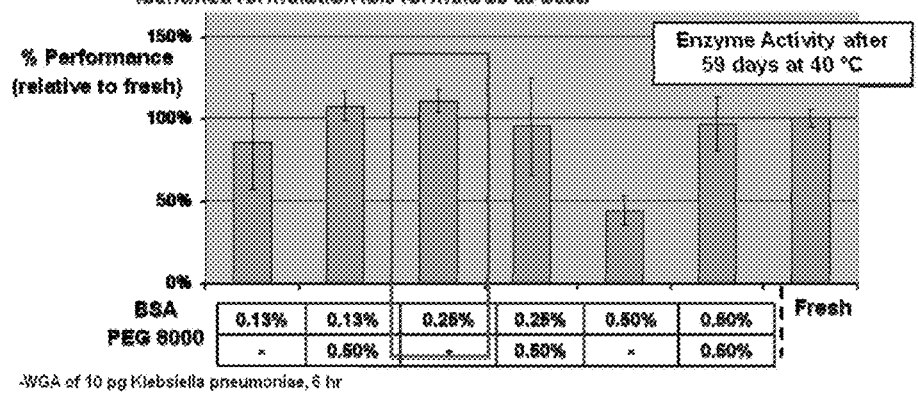
FIG. 17 shows that a number of BSA levels (0.13%-1% final concentration) as well as the addition of 0.5% (final concentration) of PEG-8000 were tested in the enzyme stabilization formulations as described in Example 1.

A number of BSA levels (0.13%-1% final concentration) as well as the addition of 0.5% (final concentration) of PEG-8000 were tested using the same general scheme described above. The results of this testing are shown in FIG. 17.

Figure 18:
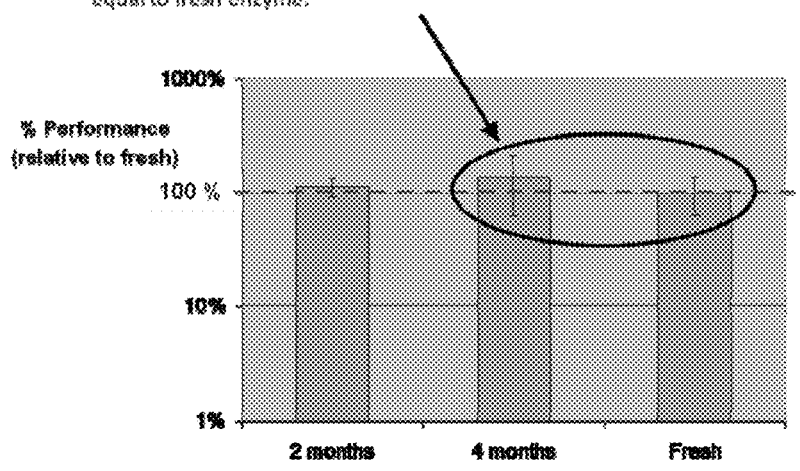
FIG. 18 shows that the lyophilized enzymes in Ibis Formula 33 when stored at room temperature for 4 months performed equal to fresh enzyme.
Figure 19:
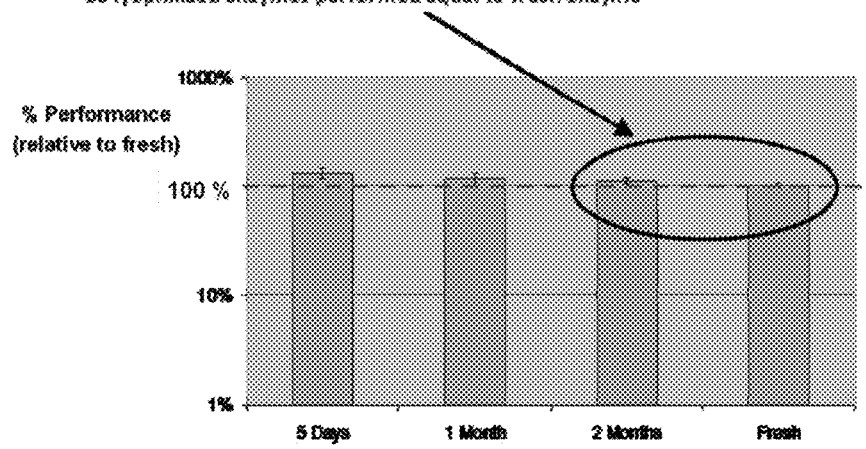
FIG. 19 shows that the lyophilized enzymes in Ibis Formula 33 performed equal to fresh enzyme after two months at 40 degrees Celsius.

Using the excipients developed in this work we successfully demonstrated that the the enzymatic activity of all three of these enzymes is maintained during lyophilization and the stability of these enzymes was dramatically increased from less than 10 days at room temperature (−25 C) to more than 2 months at 40 C. This formulation also increases the total reaction yield when compared to a fresh (i.e., stored in a −20 C freezer until use) enzyme mix. Long-term stability results for storage at room temperature are shown in FIG. 18. This figures shows that the lyophilized enzymes in Ibis Formula 33 when stored at room temperature for 4 months performed equal to fresh enzyme. FIG. 19 shows long-term storage stability using accelerated aging of 40 degrees Celsius for two months, which is equal to approximately 6 months of room temperature storage. FIG. 19 shows that the lyophilized enzymes in Ibis Formula 33 performed equal to fresh enzyme after two months at 40 degrees Celsius.

Example 2

Sample Preparation Methods

This example describes various sample preparation methods that may be used, for example, in microfluidic devices. Such methods allows the use of a single universal buffer and make it possible for the sample to remain in single tube. The general outline for such methods include the following steps: lysis and extraction; whole-genome amplification (or other amplification method); fragmentation of DNA; end polishing; ligation; removal of incomplete products; and final clean-up. Described below are certain details on a number of such steps.

i. Exemplary Fragmentation Methods

An amplified sample (e.g., WGA sample) can be fragmented with a device composed of the following components: 1) sonicator assembly: 2.4 meghaertz miniature ultrasonic nebulizer, Sonaer 241V; 2) Transducer: gold coated nebulizer crystal, Sonaer 24AU; 3) Power supply: 24 volt power supply, Sonaer ST624; and 4) Lid: machined plastic to create enclosure in sonicator assembly. Sonication using this method can be conducted for 10 minutes total time, with 50% duty cycle with intervals of 15 s on, 15 s off.

ii. Ligation Reaction Speed Optimized

The speed of the ligation was optimized from an initial condition, which allowed a significant increase in the amount of final product generated in 30 minutes. The optimization included modified buffer components or concentrations and modified enzyme concentrations. The parameters are shown in Table 1 below. The reactions conditions were 30 C, 30 minutes, and 65 C, 10 minutes.

TABLE 1

| | T4 Ligase | trehalose | (NH4)2SO4 | Tris | MgCl2 | Tween 40 | DTT |
|---|---|---|---|---|---|---|---|
| condition 1 | 3,000 units | 452 5 mM | 8 mM | 40 mM | 9.6 mM | 1% | 2.81 mM |
| optimized | 10,000 units | 452 5 mM | 8 mM | 40 mM | 9.6 mM | 1% | 2.81 mM |

| | dNTPs (each) | ATP | PEG 8000 | pH | Hairpin | Insert | WGA Primers |
|---|---|---|---|---|---|---|---|
| condition 1 | 518 uM | 3 mM | 0 | 7.6 | 4.36 uM | 0.436 uM | 35.8 uM |
| optimized | 518 uM | 334 uM | 4.55% | 7.6 | 4.36 uM | 0.436 uM | 35.8 uM |

Important parameters for optimization included: ligase concentration, ATP concentration, PEG concentration, addition of sodium pyrophosphate after 1 minute of reaction. The optimized conditions lead to a significant increase in final product after 30 minutes.

iii. WGA Enzymes in Amplification Buffer End Polish Efficiently

Conditions were examined to test end polishing efficiency. Conditions tested included: reaction time, reaction temperature, dATP concentration, DTT concentration, PEG concentration, sperimidine concentration, poly-lysine concentration. The parameters employed are shown in Table 2 below. The reaction conditions employed were: 37 C, 5 minutes; 50 C, 2 minutes; and 75 C, 10 minutes.

TABLE 2

| | Phi 29 | Klenow exo- | trehalose | (NH4)2SO4 | Tris | MgCl2 | Tween 40 |
|---|---|---|---|---|---|---|---|
| end polish | 100 units | 40 units | 452 5 mM | 8 mM | 40 mM | 9.6 mM | 1% |

| | DTT | dNTPs (each) | dATP | pH | WGA Primers | Duplex Oligo |
|---|---|---|---|---|---|---|
| end polish | 2.81 mM | 518 uM | 5 mM | 7.6 | 35.8 uM | 1 uM |

The analysis method employed was electro-spray ionization time of flight mass spectrometry (ESI-TOF MS). One important parameter fond was reaction temperature (this was an important parameter as below 55 C minimal A-tailing was observed while above 55 C significant A-tailing was observed), dATP concentration (increasing the dATP concentration increases A-tailing). The results found that 100% of the products were blunted appropriately, and approximately 70% of the ends were A-tailed.

iv. Exonuclease Clean-Up of Ligation Reactions

A ligation reaction performed using 'condition 1' shown in Table 1 above (with a slightly different hairpin/insert sequences) digested using exo III and exo VII. The hairpin and insert concentration shown below are prior to the ligation reaction. The majority of the insert was converted to "final product" during the ligation reaction. The conditions used are shown in Table 3. The reactions conditions were 37 C, 1 hr, and 70 C, 10 minutes.

TABLE 3

|  | Exo III | Exo VII | trehalose | (NH4)2SO4 | Tris | MgCl2 | Tween 40 |
| --- | --- | --- | --- | --- | --- | --- | --- |
| exo digest | 100 units | 5 units | 452 5 mM | 8 mM | 40 mM | 9.6 mM | 1% |

|  | DTT | dNTPs (each) | pH | Hairpin | Insert | WGA Primers |
| --- | --- | --- | --- | --- | --- | --- |
| exo digest | 2.81 mM | 518 uM | 7.6 | 4.36 uM | 0.436 uM | 35.8 uM |

It is noted that WGA amplification primers were included in all these reactions even though they are not part of the reaction to determine if they would cause any inhibition (none was observed.) Similarly, dNTPs were included in reactions (such as the ligation or exo digestion) even though they were not needed in the reaction to determine if they would cause any inhibition (none was observed.) The exonuclease degrades non-circularized templates, removing any DNA other than final product.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of generating a nucleic acid sequencing library, comprising:
   a) introducing a biological sample into a loading port configured for introduction of said biological sample into a microfluidic card;
   b) lysing cells in said biological sample in a lysis sub-circuit of said microfluidic card operably linked to said loading port, wherein said lysis sub-circuit comprises:
      i) a lysis chamber; and
      ii) a lysis buffer wherein said lysis sub-circuit is configured to lyse said biological sample with said lysis buffer to generate a lysed sample;
   c) extracting nucleic acid from said biological sample in a nucleic acid extraction sub-circuit of said microfluidic card operably linked to said lysis sub-circuit wherein said nucleic acid extraction sub-circuit comprises:
      i) a nucleic acid extraction component configured to bind nucleic acids present in said lysed sample;
      ii a wash buffer;
      iii) an elution buffer; and
      iv) a pump component configured for pumping said elution buffer over said nucleic acid extraction component to generate a mixture of extracted nucleic acids;
   d) amplifying said nucleic acid in an amplification sub-circuit operably linked to said nucleic acid extraction sub-circuit of said microfluidic card comprising a stabilized enzyme mixture wherein said stabilized enzyme mixture comprises at least one amplification-related enzyme useful for performing amplification of said extracted nucleic acid to generate amplified nucleic acid;
   e) fragmenting said amplified nucleic acid in a fragmentation sub-circuit operably linked to said amplification sub-circuit of said microfluidic card to generate fragmented nucleic acids wherein said fragmentation sub-circuit comprises:
      i) a reagent mixture configured for digesting said amplified nucleic acid to generate fragmented nucleic acid; and/or
      ii) a fragmentation component configured for mechanically fragmenting said amplified nucleic acid to generate said fragmented nucleic acids;
   f) polishing ends of said fragmented nucleic acids in said fragmentation sub-circuit of said microfluidic care wherein said fragmentation sub-circuit comprises at least one type of enzyme configured for polishing the ends of said fragmented nucleic acid to generate fragmented nucleic acids comprising polished ends;
   g) ligating said fragmented nucleic acids comprising said polished ends to nucleic acid linkers in a linker ligation sub-circuit operably linked to said fragmentation sub-circuit of said microfluidic card wherein said linker ligation sub-circuit comprises:
      i) nucleic acid linkers configured for use in sequencing methods; and
      ii) a ligation enzyme mixture configured for ligating said nucleic acid linkers to said fragmented nucleic acid;
   h) polishing ends of said fragmented nucleic acids ligated to said nucleic acids linkers in said linker ligation sub-circuit of said microfluidic card comprising at least one type of enzyme configured for polishing the ends of said nucleic acid sequencing library to generate a nucleic acid sequencing library comprising polished ends; and
   i) purifying said nucleic acid sequencing library comprising polished ends in a purification sub-circuit operably linked to said linker ligation sub-circuit of said microfluidic card wherein said purification sub-circuit comprises a nucleic acid purification component to generate a purified nucleic acid sequencing library.

2. The method of claim 1, wherein said amplification sub-circuit comprises an enzyme for performing whole genome amplification (WGA), polymerase chain reaction (PCR), or transcription mediated amplification (TMA).

3. The method of claim 1, wherein said amplification sub-circuit comprises an enzyme selected from the group consisting of: Phi-29 polymerase, E. coli DNA polymerase I, inorganic pyrophosphatase, or any combination thereof.

4. The method of claim 1, wherein said stabilized enzyme mixture comprises: i) BSA, ii) a sugar, and iii) at least one additional component selected from the group consisting of: an inorganic salt, a divalent metal cation, a buffering agent, an emulsifier, and a reducing agent.

5. The method of claim 1, wherein said stabilized enzyme mixture comprises: i) BSA, ii) a sugar, iii) an inorganic salt, iv) a divalent metal cation, v) a buffering agent, vi) an emulsifier, vii) and a reducing agent.

6. The method of claim 5, wherein said BSA is present at a concentration of 0.05%-3.0%, said sugar is present at a concentration of 5-35%, said inorganic salt is present at a concentration of 1 mM-25 mM, said divalent metal cation is present at a concentration of 1 mM-30 mM, said buffering agent is present at a concentration of 10 mM-100 mM, said emulsifier is present at a concentration of 0.01%-0.15%, and said reducing agent is present at a concentration of 1 mM-10 mM.

7. The method of claim 1, wherein said microfluidic card comprises a waste chamber operably linked to one or more of said lysis sub-circuit, said nucleic acid extraction sub-circuit, said amplification sub-circuit, said fragmentation sub-circuit, and/or said linker ligation sub-circuit and said purification sub-circuit.

8. The method of claim 1, wherein said microfluidic card comprises a processing instrument for passing buffers and samples.

9. The method of claim 1, comprising providing one or more sealed packages comprising one or more of said lysis buffer, said wash buffer, said elution buffer, said stabilized enzyme mixture, said reagent mixture configured for digesting said amplified nucleic acid, and said ligation enzyme mixture.

10. The method of claim 1, wherein said lysis sub-circuit, said nucleic acid extraction sub-circuit, said amplification sub-circuit, said fragmentation sub-circuit, said linker ligation sub-circuit, and said purification sub-circuit of said microfluidic card are operably linked in sequence.

11. The method of claim 1, wherein said extraction sub-circuit comprises a wash buffer and an elution buffer, and wherein said wash buffer, said elution buffer and said lysis buffer are a single buffer.

12. The method of claim 1, wherein said linker is a nucleic acid adaptor.

13. The method of claim 1, wherein said biological sample is a human sample, a patient sample, a biowarfare sample, an environmental sample, a soil sample, or a sample comprising a target genome and a background genome.

14. A method of sequencing nucleic acid, comprising:
   a) introducing a biological sample into a loading port configured for introduction of said biological sample into a microfluidic card;
   b) lysing cells in said biological sample in a lysis sub-circuit of said microfluidic card operably linked to said loading port, wherein said lysis sub-circuit comprises:
      i) a lysis chamber; and
      ii) a lysis buffer wherein said lysis sub-circuit is configured to lyse said biological sample with said lysis buffer to generate a lysed sample;
   c) extracting nucleic acid from said biological sample in a nucleic acid extraction sub-circuit of said microfluidic card operably linked to said lysis sub-circuit wherein said nucleic acid extraction sub-circuit comprises:
  i) a nucleic acid extraction component configured to bind nucleic acids present in said lysed sample;
  ii) a wash buffer;
  iii) an elution buffer; and
  iv) a pump component configured for pumping said elution buffer over said nucleic acid extraction component to generate a mixture of extracted nucleic acids;
d) amplifying said nucleic acid in an amplification sub-circuit operably linked to said nucleic acid extraction sub-circuit of said microfluidic card comprising a stabilized enzyme mixture wherein said stabilized enzyme mixture comprises at least one amplification-related enzyme useful for performing amplification of said extracted nucleic acid to generate amplified nucleic acid:
e) fragmenting said amplified nucleic acid in a fragmentation sub-circuit operably linked to said amplification sub-circuit of said microfluidic card to generate fragmented nucleic acids wherein said fragmentation sub-circuit comprises:
  i) a reagent mixture configured for digesting said amplified nucleic acid to generate fragmented nucleic acid; and/or
  ii) a fragmentation component configured for mechanically fragmenting said amplified nucleic acid to generate said fragmented nucleic acids;
f) polishing ends of said fragmented nucleic acids in said fragmentation sub-circuit of said microfluidic care wherein said fragmentation sub-circuit comprises at least one type of enzyme configured for polishing the ends of said fragmented nucleic acid to generate fragmented nucleic acids comprising polished ends;
g) ligating said fragmented nucleic acids comprising said polished ends to nucleic acid linkers in a linker ligation sub-circuit operably linked to said fragmentation sub-circuit of said microfluidic card wherein said linker ligation sub-circuit comprises:
  i) nucleic acid linkers configured for use in sequencing methods; and
  ii) a ligation enzyme mixture configured for ligating said nucleic acid linkers to said fragmented nucleic acid;
h) polishing ends of said fragmented nucleic acids ligated to said nucleic acids linkers in said linker ligation sub-circuit of said microfluidic card comprising at least one type of enzyme configured for polishing the ends of said nucleic acid sequencing library to generate a nucleic acid sequencing library comprising polished ends;
i) purifying said nucleic acid sequencing library comprising polished ends in a purification sub-circuit operably linked to said linker ligation sub-circuit of said microfluidic card wherein said purification sub-circuit comprises a nucleic acid purification component to generate a purified nucleic acid sequencing library;
j) withdrawing said purified nucleic acid sequencing library from an outlet port of said microfluidic card; and
k) introducing said purified nucleic acid sequencing library into a sequencing system.

15. The method of claim 14, wherein said sequencing system comprises chain terminator sequencing, dye terminator sequencing, amplification-based next generation sequencing, pyrosequencing, Supported Oligonucleotide Ligation and Detection (SOLiD) sequencing, non-amplification-based next generation sequencing, single molecule sequencing, nanopore sequencing, real-time sequencing by synthesis, and single molecule real time (SNRT) sequencing using zero-mode waveguides (ZMWs).

* * * * *

SEQUENCE LISTING

```
<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t or g

<400> SEQUENCE: 1
cgactcgagn nnnatgtgg                                                19
```